US011739054B2

(12) United States Patent
Janda et al.

(10) Patent No.: US 11,739,054 B2
(45) Date of Patent: Aug. 29, 2023

(54) METHODS AND COMPOSITIONS FOR SUBSTANCE USE DISORDER VACCINE FORMULATIONS AND USES THEREOF

(71) Applicant: MOLECULAR EXPRESS, INC., Rancho Dominguez, CA (US)

(72) Inventors: Kim Janda, Rancho Dominguez, CA (US); Sam On Ho, Rancho Dominguez, CA (US); Gary Fujii, Rancho Dominguez, CA (US)

(73) Assignee: MOLECULAR EXPRESS, INC., Rancho Dominguez, CA (US)

( * ) Notice: Subject to any disclaimer, the term of this patent is extended or adjusted under 35 U.S.C. 154(b) by 98 days.

(21) Appl. No.: 17/129,712

(22) Filed: Dec. 21, 2020

(65) Prior Publication Data
US 2021/0107862 A1  Apr. 15, 2021

Related U.S. Application Data

(63) Continuation of application No. 16/621,224, filed as application No. PCT/US2018/036904 on Jun. 11, 2018, now abandoned.

(60) Provisional application No. 62/517,973, filed on Jun. 11, 2017.

(51) Int. Cl.
*C07C 233/54* (2006.01)
*A61P 25/30* (2006.01)
*A61K 39/00* (2006.01)
*A61K 39/385* (2006.01)

(52) U.S. Cl.
CPC ........ *C07C 233/54* (2013.01); *A61K 39/0013* (2013.01); *A61K 39/385* (2013.01); *A61P 25/30* (2018.01); *A61K 2039/55505* (2013.01); *A61K 2039/55555* (2013.01); *A61K 2039/55561* (2013.01); *A61K 2039/6012* (2013.01); *A61K 2039/6037* (2013.01); *A61K 2039/627* (2013.01)

(58) Field of Classification Search
CPC .............. C07C 233/54; A61K 39/0013; A61K 39/385; A61K 2039/55505; A61K 2039/55555; A61K 2039/55561; A61K 2039/6012; A61K 2039/6037; A61K 2039/627; A61P 25/30; A61P 37/04
See application file for complete search history.

(56) References Cited

U.S. PATENT DOCUMENTS

| | | |
|---|---|---|
| 3,598,122 A | 8/1971 | Zaffaroni |
| 4,286,592 A | 9/1981 | Chandrasekaran |
| 4,314,557 A | 2/1982 | Chandrasekaran |
| 4,329,281 A | 5/1982 | Christenson et al. |
| 4,379,454 A | 4/1983 | Campbell et al. |
| 4,568,343 A | 2/1986 | Leeper et al. |
| 4,767,402 A | 8/1988 | Kost et al. |
| 4,780,212 A | 10/1988 | Kost et al. |
| 4,868,132 A | 9/1989 | Byrnes et al. |
| 4,897,268 A | 1/1990 | Tice et al. |
| 4,948,587 A | 8/1990 | Kost et al. |
| 5,057,540 A | 10/1991 | Kensil et al. |
| 5,075,109 A | 12/1991 | Tice et al. |
| 5,273,965 A | 12/1993 | Kensil et al. |
| 5,352,449 A | 10/1994 | Beltz et al. |
| 5,422,109 A | 6/1995 | Brancq et al. |
| 5,424,067 A | 6/1995 | Brancq et al. |
| 5,443,829 A | 8/1995 | Kensil et al. |
| 5,457,041 A | 10/1995 | Ginaven et al. |
| 5,464,387 A | 11/1995 | Haak et al. |
| 5,560,398 A | 10/1996 | Pfleger |
| 5,591,139 A | 1/1997 | Lin et al. |
| 5,618,275 A | 4/1997 | Bock |
| 5,643,575 A | 7/1997 | Martinez et al. |
| 5,656,016 A | 8/1997 | Ogden |
| 5,672,662 A | 9/1997 | Harris et al. |
| 5,679,356 A | 10/1997 | Bonnem et al. |
| 5,705,153 A | 1/1998 | Shorr et al. |
| 5,722,397 A | 3/1998 | Eppstein |
| 5,730,990 A | 3/1998 | Greenwald et al. |
| 5,763,189 A | 6/1998 | Buechler et al. |
| 5,876,727 A | 3/1999 | Swain et al. |
| 5,885,211 A | 3/1999 | Eppstein et al. |
| 5,902,588 A | 5/1999 | Greenwald et al. |
| 5,932,462 A | 8/1999 | Harris et al. |
| 6,018,678 A | 1/2000 | Mitragotri et al. |
| 6,033,928 A | 3/2000 | Eriguchi et al. |

(Continued)

FOREIGN PATENT DOCUMENTS

| | | |
|---|---|---|
| EP | 0480981 B1 | 10/1993 |
| EP | 0480982 B2 | 10/1993 |

(Continued)

OTHER PUBLICATIONS

Tsuchikama K, An Z. Antibody-drug conjugates: recent advances in conjugation and linker chemistries. Protein Cell. Oct. 2016;9(1):33-46 (Year: 2016).*

(Continued)

*Primary Examiner* — Brandon J Fetterolf
*Assistant Examiner* — Lauren Wells
(74) *Attorney, Agent, or Firm* — Acuity Law Group, PC; Michael A. Whittaker

(57) ABSTRACT

The present invention relates to vaccine compositions for treatment of substance use disorders, methods for the manufacture thereof, and methods for the use thereof to treat an animal. These compositions comprise a hapten conjugated via a linker to a protein scaffold and mixed with a particulate carrier and at least one immunostimulatory adjuvant molecule.

9 Claims, 11 Drawing Sheets

(56) References Cited

U.S. PATENT DOCUMENTS

| | | | |
|---|---|---|---|
| 6,238,931 | B1 | 5/2001 | Buechler et al. |
| 6,251,687 | B1 | 6/2001 | Buechler et al. |
| 6,322,532 | B1 | 11/2001 | D'Sa et al. |
| 6,676,961 | B1 | 1/2004 | Lichter |
| 6,685,699 | B1 | 2/2004 | Eppstein et al. |
| 6,871,477 | B1 | 3/2005 | Tucker |
| 6,908,453 | B2 | 6/2005 | Fleming et al. |
| 6,970,739 | B1 | 11/2005 | Inoue |
| 6,974,588 | B1 | 12/2005 | Miranda et al. |
| 7,018,345 | B2 | 3/2006 | Mori et al. |
| 7,033,598 | B2 | 4/2006 | Lerner |
| 7,402,572 | B2 | 7/2008 | Krieg et al. |
| 2002/0004208 | A1 | 1/2002 | Ennifar et al. |
| 2007/0238653 | A1* | 10/2007 | Owens .................. A61K 31/13 514/17.7 |
| 2009/0305995 | A1 | 12/2009 | Krawinkler et al. |
| 2020/0115324 | A1 | 4/2020 | Janda et al. |

FOREIGN PATENT DOCUMENTS

| | | |
|---|---|---|
| EP | 0399843 B1 | 7/1994 |
| EP | 0382271 B1 | 12/1994 |
| GB | 2232892 A | 1/1991 |
| WO | 9014837 A1 | 12/1990 |
| WO | 9508772 A1 | 3/1995 |
| WO | 9517210 A1 | 6/1995 |
| WO | 9602555 A1 | 2/1996 |
| WO | 9856414 A1 | 12/1998 |
| WO | 9911241 A1 | 3/1999 |
| WO | 9912565 A1 | 3/1999 |
| WO | 2018231706 A1 | 12/2018 |

OTHER PUBLICATIONS

Adler et al., Virus-Like Particles from Killer, Neutral, and Sensitive Strains of *Saccharomyces cerevisiae*. J Virol.Feb. 1976;17(2):472-476.

Association, A.H., 2005 American Heart Association guidelines for cardiopulmonary resuscitation and emergency cardiovascular care: Part 10.2: toxicology in ECC. Circulation, 2005. 112: p. IV126-IV132.

Bertol et al., Cocaine-related deaths: an enigma still under investigation. Forensic Sci Int. Apr. 7, 2008; 176(2-3):121-123.

Boehm et al., Cellular Responses to Interferon-Gamma. Annu Rev Immunol. 1997;15:749-795.

Bremer et al., Injection Route and TLR9 Agonist Addition Significantly Impact Heroin Vaccine Efficacy. Mol Pharm. Mar. 3, 2014;11(3):1075-1080.

Byrnes-Blake et al., Generation of anti-(+)methamphetamine antibodies is not impeded by (+)methamphetamine administration during active immunization of rats. Int Immunopharmacol. Feb. 2001;1(2):329-338.

Carroll and Onken, Behavioral Therapies for Drug Abuse. Am J Psychiatry. Aug. 2005;162(8):1452-1460.

Carroll et al., Synthesis of Mercapto (+) methamphetamine Haptens and Their Use for Obtaining Improved Epitope Density on (+) Methamphetamine Conjugate Vaccines. J Med Chem. Jul. 28, 2011;54(14):5221-5228.

Castro et al., Cocaine and Methamphetamine: Differential Addiction Rates. Psychol Addict Behav. Dec. 2000;14(4):390-396.

Chang et al., Granulocyle-Macrophage Colony Stimulating Factor: An Adjuvant for Cancer Vaccines. Hematology. Jun. 2004;9(3):207-215.

Chen and Chen, The Development of Antibody-based Immunotherapy for Methamphetamine Abuse: Immunization, and Virus-Mediated Gene Transfer Approaches Curr Gene Ther. Feb. 2013;13(1):39-50.

Collins et al., Lipid tucaresol as an adjuvant for methamphetamine vaccine development Chem Commun (Camb). Apr. 21, 2014;50(31):4079-4081.

Collins et al., Methamphetamine Vaccines: Improvement through Hapten Design. J Med Chem. Apr. 28, 2016;59(8):3878-3885.

Comer et al., Abuse Liability of Prescription Opioids Compared to Heroin in Morphine-Maintained Heroin Abusers. Neuropsychopharmacology. Apr. 2008;33(5):1179-1191.

De Villiers et al., Nicotine hapten structure, antibody selectivity and effect relationships: Results from a nicotine vaccine screening procedure. Vaccine. Mar. 2, 2010;28(10):2161-2168.

Dranoff, GM-CSF-based Cancer Vaccines. Immunol Rev. Oct. 2002;188:147-154.

Duryee et al., Immune responses to methamphetamine by active immunization with peptide-based, molecular adjuvant-containing vaccines. Vaccine. May 14, 2009;27(22):2981-2988.

Fattom et al., Laboratory and Clinical Evaluation of Conjugate Vaccines Composed of *Staphylococcus aureus* Type 6 and Type 8 Capsular Polysaccharides Bound to Pseudomonas Aeruginosa Recombinant Exoprotein A. Infect Immun. Mar. 1993;61(3):1023-1032.

Fujii et al., The Formation of Amphotericin B Ion Channels in Lipid Bilayers. Biochemistry. Apr. 22, 1997;36(16):4959-4968.

Fujii et al., The VesiVax system: a method for rapid vaccine development. Front Biosci. Jan. 1, 2008 ;13:1968-1980.

Gibson et al., Nonpeptidic av beta3 Integrin Antagonist Libraries: On-Bead Screening and Mass Spectrometric Identification Without Tagging. Angew Chem Int Ed Engl Jan. 5, 2001;40(1):165-169.

Goebel et al., Studies on Antibacterial Immunity Induced by Artificial Antigens : I. Immunity to Experimental Pneumococcal Infection with an Antigen Containing Cellobiuronic Acid. J Exp Med. Feb. 28, 1939;69(3):353-364.

Gonzales et al., The Methamphetamine Problem in the United States. Annu. Rev Public Health, 2010;31(1):385-398.

Gooyit et al., Influencing Antibody-Mediated Attenuation of Methamphetamine CNS Distribution through Vaccine Linker Design. ACS Chem Neurosci. Mar. 2017;8(3):468-472.

Gottschling et al., Cellular solid-phase binding assay and mass spectrometry for screening of a4beta7 integrin antagonists. Bioorg Med Chem Lett Dec. 3, 2001; 11 (23):2997-3000.

Hewitt and Adler, Murine immunosuppression with mycoviral dsRNA. Immunopharmacology. Dec. 1982;5(2):103-109.

Hollander, The management of cocaine-associated myocardial ischemia. N Engl J Med.. Nov. 9, 1995;333(19):1267-1272.

Iwasaki and Medzhitov, Toll-like Receptor Control of the Adaptive Immune Responses. Nat Immunol. Oct. 2004;5(10):987-995.

Jones, Heroin use and heroin use risk behaviors among nonmedical users of prescription opioid pain relievers—United States, 2002-2004 and 2008-2010 Drug Alcohol Depend, 2013. 132(1-2): p. 95-100.

Kilmer et al., What America's Users Spend on Illegal Drugs: 2000-2010. Santa Monica, CA: RAND Corporation, 2014. https://www.rand.org/pubs/research_reports/RR534.html.

Klinman, Adjuvant Activity of CpG Oligodeoxynucleotides. Int Rev Immunol. May-Aug. 2006;25(3-4):135-154.

Lange and Hillis, Cardiovascular Complications of Cocaine Use. N Engl J Med. 2001; 345:351-358.

Lemus and Karol, Conjugation of Haptens. In Methods Mol Med Allergy Meth Prot, edited by Jones and Lympany, Humana Press Inc. NJ. oc 2008;138:167-182.

Leon et al., Evaluation of resins for on-bead screening: A study of papain and chymotrypsin specificity using pega-bound combinatorial peptide libraries. Bioorg Med Chem Lett. Nov. 3, 1998;8(21):2997-3002.

Lin et al., Present Status of the Use of Cytokines as Adjuvants With Vaccines to Protect Against Infectious Diseases. Clin Infect Dis. Dec. 1995;21(6):1439-1449.

Maglione et al., Correlates of Outpatient Drug Treatment Drop-Out Among Methamphetamine Users. J Psychoactive Drugs. Apr.-Jun. 2000;32(2):221-228.

Marbella, Trying to prevent heroin deaths one shot at a time. The Baltimore Sun, 2014 ; accessed online at: http://www.baltimoresun.com/news/maryland/sun-investigates/bs-md-heroin-narcan-naloxone-20140906-story.html (14 pages).

Mark et al., The economic costs of heroin addiction in the United States. Drug Alcohol Depend. Jan. 1, 2001 ;61(2):195-206.

(56) References Cited

OTHER PUBLICATIONS

Maurice et al., Sigma(1) (sigma(1)) receptor antagonists represent a new strategy against cocaine addiction and toxicity. Neurosci Biobehav Rev. Jun. 2002;26(4):499-527.

McCord et al., Management of Cocaine-Associated Chest Pain and Myocardial Infarction: A Scientific Statement From the American Heart Association Acute Cardiac Care Committee of the Council on Clinical Cardiology. Circulation. Apr. 8, 2008;117(14):1897-1907.

McKetin et al., Evaluating the impact of community-based treatment options on methamphetamine use: findings from the Methamphetamine Treatment Evaluation Study (MATES). Addiction. Nov. 2012;107{11 ):1998-2008.

Menon et al Central Sympatholysis as a Novel Countermeasure for Cocaine-Induced Sympathetic Activation and Vasoconstriction in Humans. J Am Coll Cardiol. Aug. 14, 2007;50(7):626-633.

Miller et al., A Methamphetamine Vaccine Attenuates Methamphetamine-Induced Disruptions in Thermoregulation and Activity in Rats. Biol Psychiatry. Apr. 15, 2013;73(8):721-728.

Moreno et al, Impact of Distinct Chemical Structures for the Development of a Methamphetamine Vaccine. J Am Chem Soc. May 4, 2011;133(17):6587-6595.

Nelson, IL-2, Regulatory T Cells, and Tolerance. J Immunol. Apr. 1, 2004;172(7):3983-3988.

Nicosia et al., The Economic Cost of Methamphetamine Use in the United States, 2005, in The Economic Cost of Methamphetamine Use in the United States, 2005. ocRAND Corporation, Santa Monica, CA, 2009 (171 pages).

NIDA (The National Institute on Drug Abuse), Heroin. In Research Report Series, U.S. Department of Health and Human Services | National Institutes of Health. 2014:1-8.

Drain and Bradley, Solid phase synthesis of trypanothione reductase inhibitors-towards single bead screening. Tetrahedron Lett. 2001 ;42(3):515-518.

Papanikos et al., Alpha-Ketocarbonyl Peptides: A General Approach to Reactive Resin-Bound Intermediates in the Synthesis of Peptide Isosteres for Protease Inhibitor Screening on Solid Support. J Am Chem Soc. Mar. 14, 2001;123(10):2176-2181.

Portielje et al., IL-12: A Promising Adjuvant for Cancer Vaccination. Cancer Immunol Immunother. Mar. 2003;52(3):133-144.

Pryde et al., Selection of a Novel Anti-Nicotine Vaccine: Influence of Antigen Design on Antibody Function in Mice. PLOS ONE, 2013;8(10): e76557, pp. 1-16.

Rawson et al., Will the methamphetamine problem go away? J Addict Dis. 2002;21(1):5-19.

Reyes et al., KATP channels confer survival advantage in cocaine overdose. Mol Psychiatry, Dec. 2007;12(12):1060-1061.

Reyes et al., Therapeutic benefit of a KATP-channel opening drug in cocaine toxicity. Clin Pharmacol Ther. 2005;77(2): p. 99-p. 99.

Rosenblum et al., Prescription opioid abuse among enrollees into methadone maintenance treatment. Drug Alcohol Depend. Sep. 6, 2007;90(1 ):64-71.

Ruedi-Bettschen et al., Vaccination Protects Rats from Methamphetamine-induced Impairment of Behavioral Responding for Food. Vaccine. Sep. 23, 2013;31(41):4596-4602.

SAMHSA, Results from the 2011 National Survey on Drug Use and Health: Summary of National Findings. NSDUH Series H-44, HHS Publication No. (SMA) 12-4713. Substance Abuse and Mental Health Services Administration: Rockville, MD. 2012 (78 pages).

SAMHSA, Results from the 2012 National Survey on Drug Use and Health: Summary of National Findings. NSDUH Series H-46, HHS Publication No. (SMA) 13-4795. Substance Abuse Mental Health Services Administration, Rockville, MD:2013 (178 pages).

SAMHSA, The DAWN Report: Highlights of the 2009 Drug Abuse Warning Network (DAWN) Findings on Drug-Related Emergency Department Visits. Substance Abuse and Mental Health Services Administration, Center for Behavioral Health Statistics and Quality: Rockville, MD. 2010 (8 pages).

Sharkey et al., Cocaine binding at sigma receptors. Eur J Pharmacol. Apr. 27, 1988;149(1-2):171-174.

Shen et al., A vaccine against methamphetamine attenuates its behavioral effects in mice. Drug Alcohol Depend. Apr. 1, 2013;129( (1-2): p. 41-48.

Smith and Bradley, Comparison of Resin and Solution Screening Methodologies in Combinatorial Chemistry and the Identification of a 100 nM Inhibitor of Trypanothione Reductase. J Comb Chem. Jul.-Aug. 1999;1 (4 ):326-332.

Stoute et al., A Preliminary Evaluation of a Recombinant Circumsporozoite Protein Vaccine Against Plasmodium Falciparum Malaria. RTS,S Malaria Vaccine Evaluation Group. N Engl J Med. Jan. 9, 1997;336(2):86-91.

Sulzer et al., Mechanisms of neurotransmitter release by amphetamines: A review. Prog Neurobiol. Apr. 2005;75 (6):406-433.

Taylor, Cytokines as Adjuvants for Vaccines: Antigen-Specific Responses Differ From Polyclonal Responses. Infect Immun. Sep. 1995;63{9}:3241-3244.

Theofilopoulos et al., Type I Interferons (alpha/beta) in Immunity and Autoimmunity. Annu Rev Immunol. 2005;23:307-336.

Topchieva et al., Synthesis and Physicochemical Properties of Protein Conjugates With Water-Soluble Poly (alkylene Oxides). Bioconjug Chem. Jul.-Aug. 1995;6(4):380-388.

Trinchieri, Interleukin-12 and the Regulation of Innate Resistance and Adaptive Immunity. Nat Rev Immunol. Feb. 2003;3(2):133-146.

Vocci and Appel, Approaches to the development of medications for the treatment of methamphetamine dependence. Addiction. Apr. 2007; 102 Suppl 1:96-106.

Vongpatanasin et al., Cocaine Stimulates the Human Cardiovascular System via a Central Mechanism of Action. Circulation. Aug. 3, 1999;100(5):497-502.

Walsh et al., The Relative Abuse Liability of Oral Oxycodone, Hydrocodone and Hydromorphone Assessed in Prescription Opioid Abusers. Drug Alcohol Depend. Dec. 1, 2008;98(3):191-202.

Ward et al., Binding Activities of a Repertoire of Single Immunoglobulin Variable Domains Secreted From *Escherichia coli*. Nature. Oct. 12, 1989;341(6242):544-546.

WHO Report on the Global Tobacco Epidemic, 2011: Warning about the dangers of tobacco. WHO: Geneva 2011, (164 pages).

Wilson et al., Simplified conjugation chemistry for coupling peptides to f(ab') fragments: autologous red cell agglutination assay for HIV-1 antibodies. J Immunol Methods. Oct. 14, 1994;175(2):267-273.

Yarmush et al., Coupling of Antibody-Binding Fragments to Solid-Phase Supports: Site-Directed Binding of F(ab')2 Fragments. J Biochem Biophys Methods. Dec. 1992;25(4):285-297.

International Search Report and Written issued on PCT/US2018/ 036904 dated Sep. 10, 2018 (9 pages).

International Preliminary Report on Patentability issued in PCT/ US2018/036904 dated Dec. 26, 2019 (7 pages).

* cited by examiner

R is preferably a maleimide, an alkyl halide, an aryl halide, an alpha-haloacyl, an activated aryl, a pyridyl disulfide, a carbonyl, a carboxyl, a thiol, a thioester, disulfide, a N-hydroxy-succinimide, or a cyclic thiolactone

METHODS AND COMPOSITIONS FOR SUBSTANCE USE DISORDER VACCINE FORMULATIONS AND USES THEREOF The present invention is a continuation of U.S. patent application Ser. No. 16/621,224, filed, which is the U.S. national phase of International Patent Application No. PCT/US2018/036904, filed Jun. 11, 2018, which designated the United States and claims the benefit of U.S. provisional application No. 62/517,973, filed Jun. 11, 2017, each of which is hereby incorporated by reference in their entirety including all tables, figures, and claims.

STATEMENT AS TO FEDERALLY SPONSORED RESEARCH

In some instances, the U.S. Government may have a paid-up license in this invention and the right in limited circumstances to require the patent owner to license others on reasonable terms as provided for by the terms of National Institute on Drug Abuse (NIDA) grant R41DA040422 and the National Institute of Infectious Diseases (NIAID) grant R44AI094770.

BACKGROUND OF THE INVENTION

The following discussion of the background of the invention is merely provided to aid the reader in understanding the invention and is not admitted to describe or constitute prior art to the present invention.

Substance use disorder and addiction causes significant morbidity and mortality in the United States and throughout the world and contributes significantly to crime, hospitalization rates, and treatment costs. The projected cost burden on society caused by drug addiction and abuse is estimated to be more than $600 billion. Collectively, there are several classes of drugs that contribute to substance use disorders. Brief descriptions of the most commonly abused drugs are provided below.

Opioids such as heroin has become an even more visible problem for society because of a dramatic increase in the use of opioids that are relatively easy to obtain (e.g., oxycontin and vicodin) by prescription. These opioids have been shown to lead to subsequent heroin abuse. There has also been an alarming increase in the number of deaths caused by heroin overdose fueled primarily by the introduction of more potent formulations of heroin that are being sold out on the street. In some regions of the US, deaths due to heroin overdose now account for over 50% of all drug overdose deaths combined. In response to the increasing death rate from heroin overdose, public health officials are calling for the implementation of a controversial plan to train heroin abusers to self-administer naloxone to prevent death from heroin overdose. While this plan might serve as a stopgap means of lowering the death rate caused by heroin abuse, better solutions need to be devised in order to address the heroin addiction problem.

Based on self-reported users in the US, heroin dependence doubled from 214,000 in 2002 to 467,000 in 2012, and estimates of the number of chronic heroin users from the Office of National Drug Control Policy increased from 1.2 million in 2005 to 1.5 million in 2010. The widespread prevalence of opioid abuse is of significant cost to both users and society as a whole. Heroin expenditures have grown steadily since 2006 to an estimated $27 billion in 2010 on drug purchases alone. Other negative impacts of heroin use include HIV or HCV infection, for which injection drug users remain at the highest risk. Considering criminal activities, productivity losses and medical care, heroin addiction adds an estimated $22 billion additional cost burden to the US annually. Importantly, within the last decade, non-medical use of opioid pain relievers (OPRs) containing oxycodone (Percocet, OxyContin), hydrocodone (Vicodin) or hydromorphone (Dilaudid) has become an epidemic, with the number of individuals seeking treatment for addiction to OPRs increasing from 360,000 in 2002 to 973,000 in 2012. It has been shown that the abuse liability profile among OPRs containing oxycodone, hydrocodone, fentanyl, or hydromorphone is similar to that observed in heroin and morphine. Moreover, evidence suggests that abuse of OPRs acts as a "gateway drug" to heroin use. A 2007 study found that 33% of abusers of OPRs had used heroin and that 67% of heroin users had begun opioid use by abusing OPRs.

Tobacco smoking is the leading preventable cause of death in the United States, and accounts for 10% of global mortality. As an alkaloid from tobacco leaves, (S)-nicotine is the most widely used legal stimulant and is available in many forms such as cigarettes, cigars, pipe tobacco, chewing tobacco and more recently, electronic cigarettes. Nicotine is highly addictive despite association with multiple diseases. According to a 2011 report by the National Survey on Drug Use and Health (NSDUH), the rate of cigarette use among persons aged 18 to 34 years was 30-35%. A great deal of evidence supports the view that people continue to smoke due to the addictive effects of nicotine. In addition, tobacco smoking has been irrevocably linked to a number of serious diseases such as coronary heart disease, chronic obstructive pulmonary disease (COPD), stroke, vascular disease, chronic lung diseases, and cancer. Cigarette smoking at present is considered the leading cause of preventable death in the United States. Despite knowledge of these adverse effects, nicotine addiction has historically been one of the hardest to break.

Traditional pharmacotherapeutic treatment of substance abuse disorders relies upon the use of compounds with distinct neurological activity such as receptor ligands or mimetics of endogenous signaling molecules. Examples of smoking cessation aids are nicotine replacement therapy (NRT), the antidepressant bupropion, and the nicotinic receptor partial agonist varenicline (Chantix). However, these cessation aids are only marginally effective, and, in the case of varenicline, postmarketing surveillance has raised concerns over severe neuropsychiatric side effects. The obvious flaws with such approaches are the drug-like qualities of the therapeutics themselves and the high risk of side effects related to enhanced signaling along the monoaminergic pathway. Thus, presently available aids for smoking cessation have significant shortcomings and therefore, there is a need for alternative and improved treatments.

Cocaine abuse represents a major medical and societal hazard in the US. In the 2011 report by the NSDUH, there were comparatively high and steady levels of domestic cocaine use, which included 2 million current cocaine users aged 18 to 25 years, or 1.4% of the population. In a recent Drug Abuse Warning Network (DAWN) report, 43% of illicit drug-related emergency department visits were attributed to cocaine. Despite this, there is no effective pharmacotherapy or 'antidote' for severe cocaine-induced toxicity or chronic addiction. Instead, current treatment protocols center on the alleviation or abatement of cocaine-related symptomology. Cocaine use is not only costly in terms of length and quality of human life, but also in terms of hospitalization and treatments of conditions caused by the overdose including cardiovascular, respiratory, and malignant diseases. Treatments for cocaine addiction include small molecule modulators of dopaminergic signaling, NMDA receptor antagonists/partial antagonists/blockers, σ receptor antagonists, KATP channel openers, and specific classes of GABA receptor modulators. However, as discussed above, these therapies are less than ideal.

Methamphetamine abuse has been an increasing global problem over the last few decades, and was estimated to cost over $23 billion in 2005 in the US alone. This psychostimulant is arguably one of the most addictive drugs of abuse, with a rapid transition from first use to dependence. The euphoric high from methamphetamine use results from the release of multiple neurotransmitters, including serotonin, dopamine and norepinephrine. However, severe withdrawal is experienced on attempted abstinence as repeated exposure depletes levels of these neurotransmitters and damages the corresponding transporter systems, resulting in long-term brain alterations. Consequently, the relapse rate is substantial and there are currently no approved medications for methamphetamine addiction likely due to the complex neurochemistry behind the drug's psychoactive effects. Available treatments currently include behavioral therapies but these have shown limited improvement in long-term abstinence rates with few patients managing to complete the course of treatment. Clearly, new approaches are required to aid the battle against the cycle of methamphetamine abuse, by maintaining abstinence through the prevention of relapse.

One attractive therapeutic approach utilizes active immunization against drugs of abuse. This is believed to aid those who wish to quit their addiction by sequestering the drug in the event of a relapse, thus minimizing its pharmacological effects and allowing the patient to recover. Additionally, vaccination against a drug of abuse can also be effective in preventing overdoses which, especially in the case of opioids, can have lethal consequences.

Certain types of molecules, such as small haptens, are inherently poorly immunogenic or weakly immunogenic, failing to produce an antibody response under normal circumstances. In order to obviate the problems encountered with inducing an immune response with weakly immunogenic molecules, methods to enhance their immunogenicity by binding them to "carrier" molecules are typically employed. These carriers are most commonly large immunogenic proteins; the intended effect of these conjugates is to mimic the T-cell cooperative effect that occurs with naturally immunogenic molecules. In other words, the hapten bound to a carrier will elicit T-cell participation in antibody production by the T-cell's response to the presence of the determinants on the carrier. The interaction of the T and B-cells will then proceed in the usual fashion observed, as outlined above with respect to large immunogenic proteins. By engaging the T-cells with carrier determinants, B-cells will begin antibody production not only to the carrier itself, but also to the bound hapten. This approach to increasing immunogenicity of small or poorly immunogenic molecules has been utilized successfully for decades (see, e.g., Goebel, et al., J. Exp. Med. 69: 53, 1939)

As used herein, the term "hapten" refers to an antibody-producing, small molecule that elicits an immune response when conjugated to a larger molecule, in this case, a scaffold protein. When conjugated to a scaffold protein, the hapten serves to direct the adaptive antibody immune response to produce high affinity antibodies that are specific for the drug of abuse.

A "carrier" is a protein that serves as a scaffold to display a hapten. It does so by providing a framework to which one or more haptens can be conjugated that can then be recognized by the immune system when it is picked up by immune cells.

The term "linker" refers to a segment which connects the hapten to the scaffold protein. Typically, linkers can be either a linear or branched polymer such as polyethylene glycol or an alkyl chain or a peptide.

The term "particulate carrier" refers to any molecular assembly that ranges in size from about 10 nm to about 10 microns in diameter. Examples of particulate carriers commonly used for this purpose are aluminum hydroxide, aluminum phosphate or liposomes.

Immunostimulatory adjuvant molecule refers to a molecule classified as a pathogen associated molecular pattern (PAMP) that is recognized and bound by a pattern recognition receptor (PRR). The immunostimulatory adjuvant molecule can be added to the vaccine formulations of the invention in order to direct and amplify the immune response to a target antigen or hapten conjugate. The immunostimulatory adjuvant molecule itself does not evoke the immune response to it directly; rather it serves to direct the immune system to enhance the immune response against the hapten.

BRIEF SUMMARY OF THE INVENTION

It is an object of the invention to provide immunogenic formulations against drugs of abuse, methods for the manufacture thereof, and methods for the use thereof to treat substance use disorders in an animal.

In one aspect, the invention relates to a methamphetamine derivative finding use as a hapten. Thus, the present invention relates to compounds or salts thereof, said compound having a general formula:

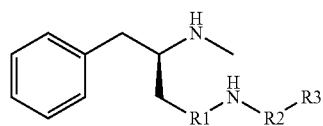

wherein

R1 is optionally substituted $C_{1-6}$ alkyl, wherein substitution(s), when present, may be independently selected from the group consisting of —$NO_2$, —$NH_2$, —OH, =O, —COOR' where R' is H or lower alkyl, —$CH_2OH$, and —$CONH_2$, R2 is peptide of m amino acid residues, an alkylene oxide of m alkylene oxide monomers, or $(CH_2)m$, where m=2 to 6; and R3 is a linkage chemistry which provides a terminal functional moiety selected from the group consisting of protected or unprotected sulfhydryl moieties, protected or unprotected amine moieties, protected or unprotected hydroxyl moieties, primary amine-reactive moieties, sulfhydryl-reactive moieties, photoreactive moieties, carboxyl-reactive moieties, arginine-reactive moieties, and carbonyl-reactive moieties.

In certain embodiments, R1 is —$(CH_2)_n$—, wherein n is 1 to 6; R2 is —$(O—CH_2—CH_2)_p$—, wherein p is 1 to 6; and/or R3 is a functional moiety selected from the group consisting of protected or unprotected sulfhydryl moieties, protected or unprotected amine moieties, protected or unprotected hydroxyl moieties, primary amine-reactive moieties, sulfhydryl-reactive moieties, photoreactive moieties, carboxyl-reactive moieties, arginine-reactive moieties, and carbonyl-reactive moieties In preferred embodiments, R2 is -Gly-Gly-, -Gly-Ala-, -Ala-Gly-, -Pro-Gly-,-Gly-Pro-, -Ala-Ala-, -Ala-Pro-, or -Pro-Ala-.

In preferred embodiments, R3 is selected from the group consisting of a maleimide, an alkyl halide, an aryl halide, an alpha-haloacyl, an activated aryl, a pyridyl disulfide, a carbonyl, a carboxyl, a thiol, a thioester, disulfide, a N-hydroxy-succinimide, or a cyclic thiolactone.

In another aspect, the invention relates to conjugates comprising a methamphetamine derivative as described above covalently bound through the functional moiety on the compound(s) to a corresponding coupling site on a protein, polypeptide, detectable label, nucleic acid, or solid phase.

In certain embodiments, the functional moiety is a sulfhydryl-reactive moiety such as a maleimide, an alkyl halide, an aryl halide, an acryl, or an $\alpha$-haloacyl, wherein the sulfhydryl-reactive moiety reacts with sulfhydryls to form thiol ether bonds. In certain other embodiments, the functional moiety is a carbonyl-reactive moiety.

In various embodiments, the detectable label may be selected from the group consisting of a hapten carrier protein comprising a T-helper epitope, an enzyme, a fluorophore, biotin, avidin, streptavidin, digoxigenin, maltose, oligohistidine, 2,4-dintrobenzene, phenylarsenate, a metal, a fluorescent or colored microsphere, a fluorescent particle, and a colored latex particle. By way of example, a hapten carrier protein comprising a T-helper epitope may be selected from the group consisting of keyhole limpet hemocyanin, bovine serum albumin, thyroglobulin, thioredoxin, ovalbumin, lysozyme, diphtheria antigen DT, diphtheria antigen CRM197 and tetanus toxoid. This list is not meant to be limiting.

In related aspects, the present invention relates to methods for preparing a conjugate, comprising contacting one or more compounds of one of claims 1-6 with a protein, polypeptide, detectable label, nucleic acid, or solid phase under conditions to provide covalent coupling of said compound(s) to said protein, polypeptide, detectable label, nucleic acid, or solid phase through a reactive moiety on the compound(s). In other related aspects, the present invention relates to methods of stimulating an immune response to methamphetamine, comprising immunizing an animal with a conjugate according to the present invention.

In one aspect, the invention relates to a vaccine composition comprising one or more haptens conjugated via a linker to a hapten carrier protein. The hapten-protein conjugate is then mixed or processed with one or more a particulate carriers and an immunostimulatory adjuvant molecule. The compositions of the present invention comprise:
 a) an aqueous vehicle;
 b) one or more haptens conjugated via a linker to a protein scaffold that is then mixed with;
 c) one or more particulate carriers and;
 d) one or more immunostimulatory adjuvant molecules In relates aspects, the invention relates to methods of stimulating an immune response to methamphetamine, comprising immunizing an animal with a vaccine composition of the present invention.

In certain embodiments, the immunostimulatory adjuvant molecules may be those that are well known in the art, such as lipopeptide, lipopolysaccharide, oligonucleotides with CpG motifs, cyclic dinucleotides, proteins and the like.

In certain embodiments, the particulate carriers are provided within a particular average size range, as size can affect the efficiency with which they are taken up by the immune system when delivered mucosally, and/or cleared when delivered systemically (e.g., subcutaneously, intramuscularly or intravenously). Particle size can be determined by methods well known in the art, including photon correlation spectroscopy, dynamic light scattering, etc. In preferred embodiments, the particulate carriers are substantially between 10 and 10,000 nm in diameter, more preferably substantially between 50 and 500 nm in diameter, and most preferably substantially between 50 and 150 nm in diameter. The term "substantially" as used herein in this context means that at least 75%, more preferably 80%, and most preferably at least 90% of the liposomes are within the designated range.

Methods for covalently conjugating the hapten via a linker to the protein scaffold are well known in the art. Chemical cross-linkers are discussed in numerous books and catalogues. See, e.g., Wong, *Chemistry of Protein Conjugation and Cross-linking*, CRC Press, Boca Raton, Fla., 1991. These reagents often employ functional groups that couple to amino acid side chains of peptides. Moieties that can be targeted using a cross-linker include primary and $\varepsilon$-amines, sulfhydryls, carbonyls, hydroxyls, and carboxylic acids. In addition, many reactive groups can be coupled nonselectively using a cross-linker such as photoreactive phenyl azides.

In another aspect, the invention relates to methods for preparing vaccine compositions. These methods comprise:
 (a) conjugating the target hapten to the protein scaffold via the linker; and
 (b) mixing with the particulate carrier; and
 (c) one or more immunostimulatory adjuvant molecules.

In another aspect, the invention relates to methods for treating an animal, preferably a mammal and most preferably a human, with formulations containing the hapten-protein conjugate. These methods comprise delivering to said animal by a systemic or mucosal route an effective amount of a vaccine formulation comprising:
 a) an aqueous vehicle;
 b) an hapten-protein conjugate;
 c) one or more particulate carriers and;
 d) one or more immunostimulatory adjuvant molecules Preferred compositions, methods for making such compositions, novel hapten designs, optimized linkers, preferred protein scaffolds, particulate carriers and immunostimulatory adjuvant molecules are discussed in detail hereinafter.

Preferred systemic routes of administration include intraperitoneal, intramuscular, subcutaneous and intradermal routes. Preferred mucosal routs of administration include oral, pulmonary, intranasal, intrarectal, intravaginal, buccal and ocular.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION OF THE INVENTION

Figure 1:
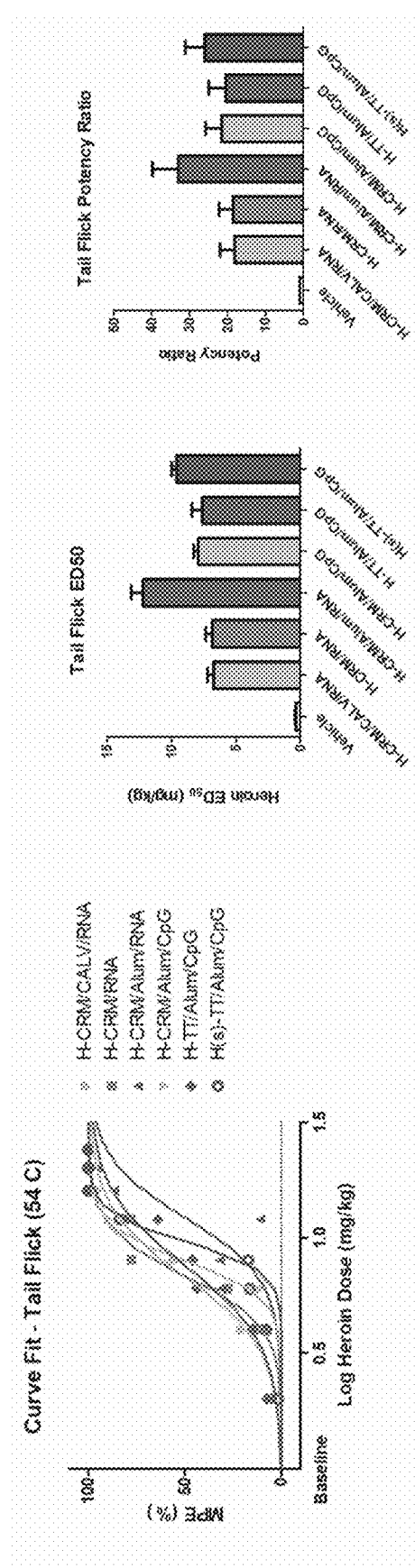
FIG. 1 depicts spinal antinociceptive responses of Hero-TT vaccine formulations measured at 45 days post-boost.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

The present invention relates in part to analogs, and most particularly methamphetamine analogs, and methods for their production and use, particularly for preparing crosslinkable analogs for conjugation to another molecule, and for use of such conjugates for preparing reagents for immunoassays that detect the parent compound and in the performance of such immunoassays e.g., as labeled conjugates. The analogs of the present invention are particularly well suited for immunization of animals to establish an immune response to the parent compound, and most particularly methamphetamine.

For the sake of clarity, definitions for the following terms regarding the compounds of the present invention are provided.

As used herein, the term "aryl" refers to an optionally substituted aromatic group with at least one ring having a conjugated pi-electron system, containing up to two conjugated or fused ring systems. Aryl includes carbocyclic aryl, heterocyclic aryl and biaryl groups, all of which may be optionally substituted. Preferably, the aryl is either optionally substituted phenyl, optionally substituted pyridyl, optionally substituted benzothiopyranyl, optionally substituted carbazole, optionally substituted naphthyl, optionally substituted tetrahydronaphthyl. While "aryl" is most preferably a monocyclic carbocyclic aromatic ring having 5 or 6 ring atoms (and is most preferably phenyl), the aryl or heteroaryl Ar group (formed into an arylene or heteroarylene in the crosslinkers described herein by elaboration from a ring atom) generally may contain up to ten ring atoms, although the skilled artisan will recognize that aryl groups with more than ten ring atoms are within the scope of the invention. The ring systems encompassed by Ar can contain up to four heteroatoms, independently selected from the group consisting of N, S, and O.

Monocyclic aryl groups include, but are not limited to: phenyl, thiazoyl, furyl, pyranyl, 2H-pyrrolyl, thienyl, pyrroyl, imidazoyl, pyrazoyl, pyridyl, pyrazinyl, pyrimidinyl, and pyridazinyl moieties. Fused bicyclic Ar groups include, but are not limited to: benzothiazole, benzimidazole, 3H-indolyl, indolyl, indazoyl, purinyl, quinolizinyl, isoquinolyl, quinolyl, phthalizinyl, naphthyridinyl, quinazolinyl, cinnolinyl, isothiazolyl, quinoxalinyl indolizinyl, isoindolyl, benzothienyl, benzofuranyl, isobenzofuranyl, and chromenyl moieties.

As used herein, the term "heteroatom" refers to non-carbon, non-hydrogen atoms such as N, O, and S.

The aryl group may also be optionally substituted by replacement of one or more hydrogen atoms by another chemical moiety. Preferred substituents include $C_{1-6}$ alkyl straight or branched (e.g. isopropyl) chain, halogen, trihalomethyl, alkoxy, $NO_2$, $NH_2$, OH, —COOR', where R' is H or lower alkyl, $CH_2OH$, and $CONH_2$.

As used herein, the term "alkyl" refers to a saturated aliphatic hydrocarbon including straight chain and branched chain groups. Preferably, the alkyl group has 1 to 20 carbon atoms. More preferably, it is a medium alkyl (having 1 to 10 carbon atoms). Most preferably, it is a lower alkyl (having 1 to 4 carbon atoms). The alkyl group may be substituted or unsubstituted.

As used herein, the term "alkoxy" group refers to both an —O-alkyl and an —O-cycloalkyl group; preferably an alkoxy group refers to a lower alkoxy, and most preferably methoxy or ethoxy.

As used herein, the term "thiolactone" refers to a cyclic hydrocarbon having 5 or 6 ring atoms, one of which is an S heteroatom, and where the heteroatom is adjacent to a carbon substituted with a =O.

As used herein, the term "thioester" refers to an organic compound having the structure R—S—C(O)—R'.

As used herein, the term "alkyl thiol" refers to an alkyl group containing an
—SH group. Thiols are also referred to as "thio alcohols" and "sulfhydryls."

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. *Fundamental Immunology*, 3rd Edition, W. E. Paul, ed., Raven Press, N.Y. (1993); Wilson (1994) *J. Immunol. Methods* 175:267-273; Yarmush (1992) *J. Biochem. Biophys. Methods* 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and $CH_1$ domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Single chain antibodies are also included by reference in the term "antibody."

The term "polypeptide" as used herein refers to a molecule having a sequence of amino acids linked by peptide bonds. This term includes proteins, fusion proteins, oligopeptides, cyclic peptides, and polypeptide derivatives. Antibodies and antibody derivatives are discussed above in a separate section, but antibodies and antibody derivatives are, for purposes of the invention, treated as a subclass of the polypeptides and derivatives. The term protein refers to a polypeptide that is isolated from a natural source, or produced from an isolated cDNA using recombinant DNA technology, and that has a sequence of amino acids having a length of at least about 200 amino acids.

The term "nucleic acids" as used herein shall be generic to polydeoxyribonucleotides (containing 2'-deoxy-D-ribose or modified forms thereof), to polyribonucleotides (containing D-ribose or modified forms thereof), and to any other type of polynucleotide which is an N-glycoside of purine or pyrimidine bases, or modified purine or pyrimidine bases.

The term "aptamer" as used herein is a single-stranded or double-stranded oligodeoxyribonucleotide, oligoribonucleotide or modified derivatives that specifically bind and alter the biological function of a target molecule. The target molecule is defined as a protein, peptide and derivatives thereof. The aptamer is capable of binding the target molecule under physiological conditions. An aptamer effect is distinguished from an antisense effect in that the aptameric effects are induced by binding to the protein, peptide and derivative thereof and are not induced by interaction or binding under physiological conditions with nucleic acid.

The term "polysaccharide" as used herein refers to a molecule comprising more than 10 glycosidically linked monosaccharide residues, while the term "oligosaccharide" refers to a molecule comprising from 2-10 glycosidically linked monosaccharide residues.

The term "small molecule" includes any molecule having a molecular weight less than about 5,000 daltons (Da), preferably less than about 2,500 Da, more preferably less than 1,000 Da, most preferably less than about 500 Da.

Functional Moieties

Chemical cross-linkers are valuable tools for preparing labeled protein and nucleic acid reagents. These reagents may be classified on the basis of the following:

1. Functional groups and chemical specificity;
2. length and composition of the cross-bridge;
3. whether the cross-linking groups are similar (homobifunctional) or different (heterobifunctional);
4. whether the groups react chemically or photochemically;
5. whether the reagent is cleavable; and
6. whether the reagent can be radiolabeled or tagged with another label.

The compounds of the present invention provide an available reactive group to act as an attachment point to a target carrier. Reactive groups on carriers that can be targeted using a cross-linker include primary amines, carbonyls, carbohydrates and carboxylic acids. In addition, many reactive groups can be coupled nonselectively using a cross-linker such as photoreactive phenyl azides. For suitable reagents, see Pierce 2003-2004 Applications Handbook and Catalog #1600926, which is hereby incorporated by reference.

Many factors must be considered to determine optimum cross-linker-to-target molar ratios. Depending on the application, the degree of conjugation is an important factor. For example, when preparing immunogen conjugates, a high degree of conjugation is normally desired to increase the immunogenicity of the antigen. However, when conjugating to an antibody or an enzyme, a low-to-moderate degree of conjugation may be optimal to ensure that the biological activity of the protein is retained. It is also important to consider the number of reactive groups on the surface of the protein. If there are numerous target groups, a lower cross-linker-to-protein ratio can be used. For a limited number of potential targets, a higher cross-linker-to-protein ratio may be required. This translates into more cross-linker per gram for a small molecular weight protein.

Conformational changes of proteins associated with a particular interaction may also be analyzed by performing cross-linking studies before and after the interaction. A comparison is made by using different arm-length cross-linkers and analyzing the success of conjugation. The use of cross-linkers with different reactive groups and/or spacer arms may be desirable when the conformation of the protein changes such that hindered amino acids become available for cross-linking.

Cross-linkers are available with varying lengths of spacer arms or bridges connecting the reactive ends. The most apparent attribute of the bridge is its ability to deal with steric considerations of the moieties to be linked. Because steric effects dictate the distance between potential reaction sites for cross-linking, different lengths of bridges may be considered for the interaction. Shorter spacer arms are often used in intramolecular cross-linking studies, while intermolecular cross-linking is favored with a cross-linker containing a longer spacer arm.

The inclusion of polymer portions (e.g., polyethylene glycol ("PEG") homopolymers, polypropylene glycol homopolymers, other alkyl-polyethylene oxides, bis-polyethylene oxides and co-polymers or block co-polymers of poly(alkylene oxides)) in cross-linkers can, under certain circumstances be advantageous. See, e.g., U.S. Pat. Nos. 5,643,575, 5,672,662, 5,705,153, 5,730,990, 5,902,588, and 5,932,462; and Topchieva et al., Bioconjug. Chem. 6: 380-8, 1995). For example, U.S. Pat. No. 5,672,662 discloses bifunctional cross-linkers comprising a PEG polymer portion and a single ester linkage. Such molecules are said to provide a half-life of about 10 to 25 minutes in water.

Designing a cross-linker involves selection of the functional moieties to be employed. The choice of functional moieties is entirely dependent upon the target sites available on the species to be crosslinked. Some species (e.g., proteins) may present a number of available sites for targeting (e.g., lysine ε-amino groups, cysteine sulfhydryl groups, glutamic acid carboxyl groups, etc.), and selection of a particular functional moiety may be made empirically in order to best preserve a biological property of interest (e.g., binding affinity of an antibody, catalytic activity of an enzyme, etc.)

Coupling through Amine Groups

Imidoester and N-hydroxysuccinimidyl ("NHS") esters are typically employed as amine-specific functional moieties. NHS esters yield stable products upon reaction with primary or secondary amines. Coupling is efficient at physiological pH, and NHS-ester cross-linkers are more stable in solution than their imidate counterparts. Homobifunctional NHS-ester conjugations are commonly used to cross-link amine-containing proteins in either one-step or two-step reactions. Primary amines are the principle targets for NHS-esters. Accessible α-amine groups present on the N-termini of proteins react with NHS-esters to form amides. However, because α-amines on a protein are not always available, the reaction with side chains of amino acids become important. While five amino acids have nitrogen in their side chains, only the ε-amino group of lysine reacts significantly with NHS-esters. A covalent amide bond is formed when the NHS-ester cross-linking agent reacts with primary amines, releasing N-hydroxysuccinimide.

Coupling Through Sulfhydryl Groups

Maleimides, alkyl and aryl halides, α-haloacyls, and pyridyl disulfides are typically employed as sulfhydryl-specific functional moieties. The maleimide group is specific for sulfhydryl groups when the pH of the reaction mixture is kept between pH 6.5 and 7.5. At pH 7, the reaction of the maleimides with sulfhydryls is 1000-fold faster than with amines. Maleimides do not react with tyrosines, histidines or methionines. When free sulfhydryls are not present in sufficient quantities, they can often be generated by reduction of available disulfide bonds.

Coupling Through Carboxyl Groups

Carbodiimides couple carboxyls to primary amines or hydrazides, resulting in formation of amide or hydrazone bonds. Carbodiimides are unlike other conjugation reactions in that no cross-bridge is formed between the carbodiimide and the molecules being coupled; rather, a peptide bond is formed between an available carboxyl group and an available amine group. Carboxy termini of proteins can be targeted, as well as glutamic and aspartic acid side chains. In the presence of excess cross-linker, polymerization may occur because proteins contain both carboxyls and amines. No cross-bridge is formed, and the amide bond is the same as a peptide bond, so reversal of the cross-linking is impossible without destruction of the protein.

Nonselective Labeling

A photoaffinity reagent is a compound that is chemically inert but becomes reactive when exposed to ultraviolet or visible light. Arylazides are photoaffinity reagents that are photolyzed at wavelengths between 250-460 nm, forming a reactive aryl nitrene. The aryl nitrene reacts nonselectively to form a covalent bond. Reducing agents must be used with caution because they can reduce the azido group.

Carbonyl Specific Cross-Linkers

Carbonyls (aldehydes and ketones) react with amines and hydrazides at pH 5-7. The reaction with hydrazides is faster than with amines, making this useful for site-specific cross-linking. Carbonyls do not readily exist in proteins; however, mild oxidation of sugar moieties using sodium metaperiodate will convert vicinal hydroxyls to aldehydes or ketones.

Hapten/Carriers

The term "hapten," as used in the present invention refers to a low-molecular weight organic compound that is not capable of eliciting an immune response by itself but will elicit an immune response once attached to a carrier molecule. In certain embodiments, the compounds used in the vaccines derived herein are haptens and are conjugated to a carrier molecule. Carrier molecules contemplated for use herein include any suitable immunogenic protein or polypeptide. A carrier protein for use herein generally comprises a molecule containing at least one T cell epitope which is capable of stimulating the T cells of the subject, which subsequently induces B cells to produce antibodies against the entire hapten-carrier conjugate molecule. The term "epitope" as used herein includes any determinant on an antigen that is responsible for its specific interaction with an antibody. Epitope may also refer to a determinant on an antigen that is recognized by T cells in the context of an MHC molecule. Epitopic determinants recognized by antibodies usually consist of chemically active surface groupings of molecules such as amino acids or sugar side chains and have specific three dimensional structural characteristics as well as specific charge characteristics. It is believed that to have immunogenic properties, a protein or polypeptide must be capable of stimulating T-cells. However, it is possible that a carrier protein that lacks a T-cell epitope may also be immunogenic.

A carrier protein is generally sufficiently foreign to elicit a strong immune response to the vaccine. Typically, the carrier protein used is a large molecule that is capable of imparting immunogenicity to a covalently-linked hapten. Illustrative carrier proteins are inherently highly immunogenic. Thus a carrier protein that has a high degree of immunogenicity and is able to maximize antibody production to the hapten is desirable.

Both bovine serum albumin (BSA) and keyhole limpet hemocyanin (KLH) have commonly been used as carriers in the development of conjugate vaccines when experimenting with animals and are contemplated herein as carrier proteins. Proteins which have been used in the preparation of therapeutic conjugate vaccines include, but are not limited to, a number of toxins of pathogenic bacteria and their toxoids. Examples include diphtheria and tetanus toxins and their medically acceptable corresponding toxoids. Other carrier protein candidates are proteins antigenically similar to bacterial toxins referred to as cross-reacting materials (CRMs).

Recombinant *Pseudomonas aeruginosa* exoprotein A (rEPA) may be used as a carrier protein because its structure and biological activities have been well characterized. Moreover, this recombinant protein has been successfully and safely used in humans in the *Staphylococcus aureus* capsular polysaccharide conjugate vaccines by the National Institutes of Health (see e.g., Fattom et al., Infect Immun. 61 1023-1032 (1993)). This protein has been identified as a suitable protein carrier because the intrinsic enzymatic activity of the native exotoxin has been eliminated due to an amino acid deletion at position 553. As a result, rEPA has the same immunological profile as the native exotoxin A (ETA), but does not possess the hepatotoxic properties of the native ETA. As used in this application, "exoprotein A" refers to a modified, non-hepatotoxic, ETA. On example of such an exoprotein A has an amino acid deletion at position 553.

Suitable carrier molecules are numerous and include, but are not limited to: Bacterial toxins or products, for example, cholera toxin B-(CTB), diphtheria toxin, tetanus toxoid, and pertussis toxin and filamentous hemagglutinin, shiga toxin, *pseudomonas* exotoxin; Lectins, for example, ricin-B subunit, abrin and sweet pea lectin; Sub virals, for example, retrovirus nucleoprotein (retro NP), rabies ribonucleoprotein (rabies RNP), plant viruses (e.g. TMV, cow pea and cauliflower mosaic viruses), vesicular stomatitis virus-nucleocapsid protein (VSV-N), poxvirus vectors and Semliki forest virus vectors; Artificial vehicles, for example, multiantigenic peptides (MAP), microspheres; Yeast virus-like particles (VLPs); Malarial protein antigen; and others such as proteins and peptides as well as any modifications, derivatives or analogs of the above. Other useful carriers include those with the ability to enhance a mucosal response, more particularly, LTB family of bacterial toxins, retrovirus nucleoprotein (retro NP), rabies ribonucleoprotein (rabies RNP), vesicular stomatitis virus-nucleocapsid protein (VSV-N), and recombinant.pox virus subunits.

To make a "direct conjugate," a hapten is directly attached to a carrier, with or without a linker. General methods for directly conjugating haptens to carrier proteins, using a homobifunctional or a heterobifunctional cross-linker are described, for example, by G. T. Hermanson in Bioconjugate Techniques, Academic Press (1996) and Dick and Beurret in Conjugate Vaccines. Contribu. Microbiol. Immunol., Karger, Basal (1989) vol. 10, 48-114. The molar ratio of hapten to protein is limited by the number of functional groups available on the protein for the specific conjugation chemistry. For example, with a carrier protein possessing n number of lysine moieties, there will be, theoretically, n+1 primary amines (including the terminal amino) available for reaction with the linker's carboxylic group. Thus, using this direct conjugation procedure the product will have a maximum of n+1 amido bonds formed, i.e., a maximum of n+1 haptens attached.

The skilled artisan will recognize that depending on the concentration of the reactants used to conjugate the hapten to the carrier protein, and the nature of the carrier protein, the ratio of hapten to carrier will vary. Also, within a given preparation of hapten-carrier conjugate, there will be variation in the hapten/carrier ratio of each individual conjugate. KLH has an abundance of lysine residues for coupling haptens allowing a high hapten: carrier protein ratio, increasing the likelihood of generating hapten-specific antibodies. Thus, different numbers of hapten can be conjugated to KLH, such as from 15 to 100 or more hapten molecules. In certain embodiments, an addictive drug hapten may be attached to a "matrix" (e.g., oligomeric and polymeric polypeptides) to increase the number of carrier protein attachment sites available. Such matrixes are described, for example, in US20020004208.

There are a large number of functional groups which can be used in order to facilitate the linking or conjugation of a carrier to a small molecule, such as a hapten. These include functional moieties such as carboxylic acids, anhydrides, mixed anhydrides, acyl halides, acyl azides, alkyl halides, N-maleimides, imino esters, isocyanates, amines, thiols, and isothiocyanates and others known to the skilled artisan. These moieties are capable of forming a covalent bond with a reactive group of a protein molecule. Depending upon the functional moiety used, the reactive group may be the E amino group of a lysine residue or a thiol group, on a carrier protein or a modified carrier protein molecule which, when reacted, results in amide, amine, thioether, amidine urea or thiourea bond formation. One skilled in the art would recognize that other suitable activating groups and conjugation techniques can be used. See, for example, Wong, Chemistry of Protein Conjugation and Cross-Linking, CRC Press, Inc. (1991). See also Hermanson, BIOCONJUGATE TECHNIQUES, Academic Press: 1996 and Dick and Beurret in Conjugate Vaccines. Contribu. Microbiol. Immunol., Karger, Basal (1989) vol. 10, 48-114. See also Methods Mol Med. 2008, 138: 167-82 for further methods for conjugation of haptens to carrier proteins.

In certain embodiments, a linker moiety is used in the conjugation of the hapten to carrier protein. In this regard, in certain embodiments, linear linker moieties are used for conjugation of haptens to carrier proteins. In other embodiments, cyclic or branched linkers are used for conjugation of haptens to carrier proteins. An illustrative linker is a succinyl moiety. Another example of a linker is ADH. A flexible tether for this purpose is described in de Villiers, S. H., et al., Vaccine, 2010. 28(10):2161-2168.

Thus, the hapten-carrier conjugates described herein for use in vaccines against addictive drugs are prepared by reacting one or more haptens with a carrier protein to yield a hapten carrier conjugate which is capable of stimulating T cells, leading to T cell proliferation and release of mediators which activate specific B cells to stimulate antibody production in response to the immunogenic hapten-carrier conjugate. Certain antibodies raised in response to the hapten carrier conjugate will be specific to the hapten portion of the hapten-carrier conjugate. The present invention contemplates the use of various suitable combinations of haptens with carrier proteins for use in the treatment of drug addiction, including nicotine addiction, cocaine addiction, methamphetamine addiction, and other drugs of addiction.

Adjuvants

Adjuvants suitable for use according to the present disclosure include any of the following. Without being bound by a theory of the invention, the adjuvants described herein are believed to target TLR4. TLR4 is unique among the TLR family in that downstream signaling occurs via both the MyD88- and TRIF-dependent pathways. Collectively, these pathways stimulate DC maturation, antigen processing/presentation, T cell priming, and the production of cytokines (e.g., IL-12, IFNa/$\beta$, and TNFa) (see, e.g., Iwasaki et al., Nat. Immunol. 5:987 (2004)). Alternatively, or in supplement, the adjuvant may be selected for its carrier properties; for example, the adjuvant may be an emulsion, a liposome, a microparticle, or alum. Adjuvants used in the art to generate an immune response include aluminum salts, such as alum (potassium aluminum sulfate), or other aluminum containing adjuvants. Additional adjuvants include QS21 and QuilA that comprise a triterpene glycoside or saponin isolated from the bark of the *Quillaja saponaria* Molina tree found in South America (see, e.g., Kensil et al., in Vaccine Design: The Subunit and Adjuvant Approach (eds. Powell and Newman, Plenum Press, N Y, 1995); U.S. Pat. No. 5,057,540), 3-DMP, polymeric or monomeric amino acids such as polyglutamic acid or polylysine. Other suitable adjuvants include oil in water emulsions (such as squalene or peanut oil) (see, e.g., Stoute et al., N. Engl. J. Med. 336, 86-91 (1997)). Another suitable adjuvant is CpG (see, e.g., Klinman, Int. Rev. Immunol. 25(3-4): 135-54 (2006); U.S. Pat. No. 7,402,572; European Patent No. 772 619).

Another class of suitable adjuvants is oil-in-water emulsion formulations (also called herein stable oil in water emulsions). Such adjuvants can be optionally used with other specific immuno stimulating agents such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™), or other bacterial cell wall components. Oil-in-water emulsions include (1) MF59 (WO 90/14837), containing 5% Squalene, 0.5% Tween 80, and 0.5% Span 85 (optionally containing various amounts of MTP-PE) formulated into submicron particles using a microfluidizer such as Model HOY microfluidizer (Microfluidics, Newton Mass.); (2) SAF, containing 10% Squalane, 0.4% Tween 80, 5% pluronic-blocked polymer L121, and thr-MDP, either microfluidized into a submicron emulsion or vortexed to generate a larger particle size emulsion, and (3) Ribi adjuvant system (RAS), (Ribi Immunochem, Hamilton, Mont.) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™). Also as described above, suitable adjuvants include saponin adjuvants, such as Stimulon™ (QS21, Aquila, Worcester, Mass.) or particles generated therefrom such as ISCOMs (immuno stimulating complexes) and ISCOMATRIX. Other adjuvants include Complete Freund's Adjuvant (CFA) (which is suitable for non-human use but is unsuitable for human use) and Incomplete Freund's Adjuvant (IFA). Other adjuvants include cytokines, such as interleukins (IL-1, IL-2, and IL-12), macrophage colony stimulating factor (M-CSF), and tumor necrosis factor (TNF).

Emulsion systems may also be used in formulating compositions of the present invention. For example, many single or multiphase emulsion systems have been described. Oil in water emulsion adjuvants per se have been suggested to be useful as adjuvant composition (EP 0 399 843B), also combinations of oil in water emulsions and other active agents have been described as adjuvants for vaccines (WO 95/17210; WO 98/56414; WO 99/12565; WO 99/11241). Other oil emulsion adjuvants have been described, such as water in oil emulsions (U.S. Pat. No. 5,422,109; EP 0 480 982 B2) and water in oil in water emulsions (U.S. Pat. No. 5,424,067; EP 0 480 981 B). The oil emulsion adjuvants for use in the present invention may be natural or synthetic, and may be mineral or organic. Examples of mineral and organic oils will be readily apparent to the man skilled in the art.

In order for any oil in water composition to be suitable for human administration, the oil phase of the emulsion system preferably comprises a metabolizable oil. The meaning of the term metabolizable oil is well known in the art. Metabolizable can be defined as "being capable of being transformed by metabolism" (Dorland's illustrated Medical Dictionary, W. B. Saunders Company, 25th edition (1974)). The oil may be any vegetable oil, fish oil, animal oil or synthetic oil, which is not toxic to the recipient and is capable of being transformed by metabolism. Nuts (such as peanut oil), seeds, and grains are common sources of vegetable oils. Synthetic oils are also part of this invention and can include commercially available oils such as NEOBEE® and others.

Squalene (2,6, 10, 15, 19,23-Hexamethyl-2,6, 10,14, 18,22-tetracosahexaene), for example, is an unsaturated oil which is found in large quantities in shark-liver oil, and in lower quantities in olive oil, wheat germ nil, rice bran oil, and yeast, and is a particularly preferred oil for use in this invention. Squalene is a metabolizable oil virtue of the fact that it is an intermediate in the biosynthesis of cholesterol (Merck index, 10th Edition, entry no.8619). Particularly preferred oil emulsions are oil in water emulsions, and in particular squalene in water emulsions. In addition, the most preferred oil emulsion adjuvants of the present invention comprise an antioxidant, which is preferably the oil alpha-tocopherol (vitamin E, EP 0 382 271 B1). WO 95/17210 and WO 99/11241 disclose emulsion adjuvants based on squalene, alpha-tocopherol, and TWEEN® 80, optionally formulated with the immuno stimulants QS21 and/or 3D-MPL (which are discussed above). WO 99/12565 discloses an improvement to these squalene emulsions with the addition of a sterol into the oil phase. Additionally, a triglyceride, such as tricaprylin (C27H50O6), may be added to the oil phase in order to stabilize the emulsion (WO 98/56414).

Examples of immunopotentiators that may be used in the practice of the methods described herein as co-adjuvants include: cyclic dinucleotides, MPL™; MDP and derivatives; oligonucleotides; double-stranded RNA; alternative pathogen-associated molecular patterns (PAMPS); saponins; small-molecule immune potentiators (SMIPs); cytokines; and chemokines.

In one embodiment, the co-adjuvant is MPL™ adjuvant, which is commercially available from GlaxoSmithKline (originally developed by Ribi ImmunoChem Research, Inc. Hamilton, Mont.). See, e.g., Ulrich and Myers, Chapter 21 from Vaccine Design: The Subunit and Adjuvant Approach, Powell and Newman, eds. Plenum Press, New York (1995). Related to MPL™ adjuvant, and also suitable as co-adjuvants for use in the compositions and methods described herein, are AS02™ adjuvant and ASO4™ adjuvant. AS02™ adjuvant is an oil-in-water emulsion that contains both MPL™ adjuvant and QS-21™ adjuvant (a saponin adjuvant discussed elsewhere herein). AS04™ adjuvant contains MPL™ adjuvant and alum. MPL™ adjuvant is prepared from lipopolysaccharide (LPS) of *Salmonella minnesota* R595 by treating LPS with mild acid and base hydrolysis followed by purification of the modified LPS.

In another embodiment, the co-adjuvant is a saponin such as those derived from the bark of the *Quillaja saponaria* tree species, or a modified saponin (see, e.g., U.S. Pat. Nos. 5,057,540; 5,273,965; 5,352,449; 5,443,829; and 5,560, 398). The product QS-21™ adjuvant sold by Antigenics, Inc. Lexington, Mass. is an exemplary saponin-containing co-adjuvant that may be used with the adjuvant of formula (I). An alternative co-adjuvant, related to the saponins, is the ISCOM™ family of adjuvants, originally developed by Iscotec (Sweden) and typically formed from saponins derived from *Quillaja saponaria* or synthetic analogs, cholesterol, and phospholipid, all formed into a honeycomb-like structure.

In yet another embodiment, the co-adjuvant is a cytokine that functions as a co-adjuvant (see, e.g., Lin et al., Clin. Infect. Dis. 21(6): 1439-49 (1995); Taylor, Infect. Immun. 63(9):3241-44 (1995); and Egilmez, Chap. 14 in Vaccine Adjuvants and Delivery Systems, John Wiley & Sons, Inc. (2007)). In various embodiments, the cytokine may be, for example, granulocyte-macrophage colony-stimulating factor (GM-CSF) (see, e.g., Change et al., Hematology 9(3): 207-15 (2004); Dranoff, Immunol. Rev. 188: 147-54 (2002); and U.S. Pat. No. 5,679,356); or an interferon, such as a type I interferon (e.g., interferon-a (IFN-a) or interferon-β (IFN-β)), or a type II interferon (e.g., interferon-γ (IFN-γ) (see, e.g., Boehm et al., Ann. Rev. Immunol. 15:749-95 (1997); and Theofilopoulos et al., Ann. Rev. Immunol. 23:307-36 (2005)); an interleukin, specifically including interleukin-1 (IL-la), interleukin-1β3 interleukin-2 (IL-2) (see, e.g., Nelson, J. Immunol. 172(7):3983-88 (2004); interleukin-4 (IL-4), interleukin-7 (IL-7), interleukin-12 (IL-12) (see, e.g., Portielje et al., Cancer Immunol. Immunother. 52(3): 133-44 (2003); and Trinchieri, Nat. Rev. Immunol. 3(2): 133-46 (2003)); interleukin-15 (11-15), interleukin-18 (IL-18); fetal liver tyrosine kinase 3 ligand (Flt3L), or tumor necrosis factor a (TNFa). The DSLP adjuvant, such as the adjuvant of formula (I), may be co-formulated with the cytokine prior to combination with the vaccine antigen, or the antigen, DSLP adjuvant (e.g., adjuvant of formula (I)), and cytokine co-adjuvant may be formulated separately and then combined.

Vaccines

In certain embodiments, methods comprise administering the vaccine composition a sufficient number of times to generate an effective antibody response to block the effects of the addictive drug. In one embodiment, the methods comprise administering the vaccine, once, or in other embodiments, more than once to the subject, in certain embodiments, exactly twice, or at least two, at least three, at least four, five, six, seven, or more times to the subject.

In certain embodiments, the methods involve administering two doses of vaccine, for example, about 3 weeks apart.

The time period between said two doses can range from about 3 weeks to 5 weeks, or be about 1 month, about 6 weeks, about 2 months, about 3 months, about 4 months, about 5 months or about 6 months.

The vaccines are administered by any parenteral delivery route known in the art such as via intramuscular, subcutaneous, or intradermal injection, or via needle-free injection. Vaccines may be formulated for any appropriate manner of administration, preferably intramuscular, subcutaneous or intradermal injection, or needle-free injection.

A liquid vaccine may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. The liquid composition can be enclosed in ampoules, disposable syringes or multiple dose vials made of glass or plastic. The use of physiological saline is preferred, and an injectable pharmaceutical composition is preferably sterile.

The amount of hapten-conjugated carrier protein in each vaccine dose is selected as an amount which induces an immunoprotective response without significant, adverse side effects in typical vaccines. Suitable dosage ranges may be determined by a skilled clinician, but are generally 0.01 to 10 mg/dose, and may be from 0.1 to 1.0 mg/dose. It generally takes a person two or more weeks to generate antibodies against a foreign antigen after a single vaccine dose, and it generally requires several vaccine doses administered over several weeks to induce high sustained antibody titers such as those desired for a vaccine against an addictive drug, such as an anti-nicotine vaccine to aid in smoking cessation. The production of antibodies in a person's blood can be monitored by using techniques that are well-known to the skilled artisan, such as ELISA, radioimmunoassay, surface plasma resonance, and Western blotting methods.

In certain embodiments, the dosage is about 1 ug/kg to about 1 mg/kg, with about 5 ug/kg to about 200 ug/kg particularly preferred. It will be evident to those skilled in the art that the number and frequency of administration will be dependent upon the response of the host. "Pharmaceutically acceptable carriers" for therapeutic use are well known in the pharmaceutical art, and are described, for example, in Remingtons Pharmaceutical Sciences, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used.

The vaccine may further comprise at least one physiologically (or pharmaceutically) acceptable or suitable excipient. Any physiologically or pharmaceutically suitable excipient or carrier (i.e., a non-toxic material that does not interfere with the activity of the active ingredient) known to those of ordinary skill in the art for use in pharmaceutical compositions may be employed in the compositions described herein. Exemplary excipients include diluents and carriers that maintain stability and integrity of proteins. Excipients for therapeutic use are well known, and are described, for example, in Remington: The Science and Practice of Pharmacy (Gennaro, 21st Ed. Mack Pub. Co., Easton, Pa. (2005)), and are described in greater detail herein.

"Pharmaceutically acceptable carriers" for therapeutic use are well known in the pharmaceutical art, and are described, for example, in Remingtons Pharmaceutical Sciences, Mack Publishing Co. (A. R. Gennaro edit. 1985). For example, sterile saline and phosphate buffered saline at physiological pH may be used. In a composition intended to be administered by injection, one or more of a surfactant, preservative, wetting agent, dispersing agent, suspending agent, buffer, stabilizer, antioxidants and/or isotonic agents may be included. For example, sodium benzoate, sorbic acid and esters of p hydroxybenzoic acid may be added as preservatives.

"Pharmaceutically acceptable salt" refers to salts of the compounds of the present invention derived from the combination of such compounds and an organic or inorganic acid (acid addition salts) or an organic or inorganic base (base addition salts). The compositions of the present invention may be used in either the free base or salt forms, with both forms being considered as being within the scope of the present invention.

The vaccines may be in any form which allows administration to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal (e.g., as a spray). The term parenteral as used herein includes iontophoretic (e.g., U.S. Pat. Nos. 7,033,598; 7,018,345; 6,970,739), sonophoretic (e.g., U.S. Pat. Nos. 4,780,212; 4,767,402; 4,948,587; 5,618,275; 5,656,016; 5,722,397; 6,322,532; 6,018,678), thermal (e.g., U.S. Pat. Nos. 5,885,211; 6,685,699), passive transdermal (e.g., U.S. Pat. Nos. 3,598,122; 3,598,123; 4,286,592; 4,314,557; 4,379,454; 4,568,343; 5,464,387; UK Pat. Spec. No. 2232892; U.S. Pat. Nos. 6,871,477; 6,974,588; 6,676,961), microneedle (e.g., U.S. Pat. Nos. 6,908,453; 5,457,041; 5,591,139; 6,033,928) administration and also subcutaneous injections, intravenous, intramuscular, intrasternal, intracavernous, intrathecal, intrameatal, intraurethral injection or infusion techniques. In a particular embodiment, a composition as described herein (including vaccine and pharmaceutical compositions) is administered intradermally by a technique selected from iontophoresis, microcavitation, sonophoresis or microneedles.

The vaccine is formulated so as to allow the active ingredients contained therein to be bioavailable upon administration of the composition to a patient. Vaccines that will be administered to a patient take the form of one or more dosage units, where for example, a vial or other container may contain a single or multiple dosage units.

A liquid pharmaceutical composition such as a vaccine, whether in the form of a solution, suspension or other like form, may include one or more of the following carriers or excipients: sterile diluents such as water for injection, saline solution, preferably physiological saline, Ringer's solution, isotonic sodium chloride, or buffers. Neutral buffered saline or saline mixed with nonspecific serum albumin are exemplary appropriate diluents. The vaccine may also contain fixed oils such as squalene, squalane, mineral oil, a mannide monooleate, cholesterol, and/or synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose; low molecular weight (less than about 10 residues) polypeptides, proteins, amino acids, carbohydrates including glucose, sucrose or dextrins, chelating agents such as EDTA, glutathione and other stabilizers and excipients. Preferably, product may be formulated as a lyophilizate using appropriate excipient solutions (e.g., sucrose) as diluents. The vaccine or components thereof can be enclosed in ampoules, disposable syringes or multiple dose vials made of glass or plastic.

It may also be desirable to include other components in a vaccine or pharmaceutical composition, such as delivery vehicles including but not limited to aluminum salts, water-in-oil emulsions, biodegradable oil vehicles, oil-in-water emulsions, biodegradable microcapsules, and liposomes. Examples of additional immuno stimulatory substances (co-adjuvants) for use in such vehicles are also described above and may include N-acetylmuramyl-L-alanine-D-isoglutamine (MDP), glucan, IL 12, GM CSF, gamma interferon and IL 12.

While any suitable carrier known to those of ordinary skill in the art may be employed in the pharmaceutical compositions of this invention, the type of carrier will vary depending on the mode of administration and whether a sustained release is desired. For parenteral administration, such as subcutaneous injection, the carrier preferably comprises water, saline, alcohol, a fat, a wax or a buffer. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109. In this regard, it is preferable that the microsphere be larger than approximately 25 microns.

The vaccines of the present invention are useful for the treatment of addiction to a variety of addictive drugs. A therapeutically effective amount of the vaccines described herein is one that induces a drug-specific antibody response that blocks the addictive drug from passing the blood-brain barrier, thereby reducing or eliminating the drug-induced alterations in brain chemistry, which is the source of drug-addiction. In this regard, it is important that the drug-carrier conjugate elicit the production of antibodies that will recognize the native drug molecule. Thus, the present invention provides in one aspect a method of treating or preventing drug addiction in a patient in need of such treatment comprising administering a therapeutically effective amount of an addictive drug hapten-carrier conjugate, optionally in combination with adjuvant, as described herein. In one embodiment, the present invention also provides methods for treating drug addiction in a patient in need of such treatment comprising administering a therapeutically effective amount of antibody raised in response to the addictive drug hapten-carrier conjugates.

Kits may contain one or more doses of adjuvant compositions, and optionally one or more doses of compositions containing addictive drug antigen(s)/hapten/hapten-carrier protein conjugate. A kit may also contain instructions. Instructions typically describe methods for administration, including methods for determining the proper state of the subject, the proper dosage amount, and the proper administration method, for administering the composition. Instructions can also include guidance for monitoring the subject over the duration of the treatment time.

Kits provided herein also can include devices for administration of each of the compositions described herein to a subject. Any of a variety of devices known in the art for administering medications or vaccines can be included in the kits provided herein. Exemplary devices include, but are not limited to, a hypodermic needle, an intravenous needle, a catheter, a needle-less injection device, an aerosolizer, inhaler or nebulizer or atomizer or microspray device, and a liquid dispenser, such as an eyedropper. Typically, the device for administering a composition is compatible with the active components of the kit. For example, a needle-less injection device, such as a high pressure injection device can be included in kits with vector particles, polynucleotides, and polypeptides not damaged by high pressure injection, but is typically not included in kits that include vector particles, polynucleotides, and polypeptides that may be damaged by high pressure injection.

Solid-Phase Immobilization

The analogs and/or conjugates of the present invention can be immobilized on solid-phase matrices for use as affinity supports or for sample analysis. Similarly, antibodies or their binding fragments made or selected using the analogs and/or conjugates of the present invention can also be immobilized on solid-phase matrices. The term "solid phase" as used herein refers to a wide variety of materials including solids, semi-solids, gels, films, membranes, meshes, felts, composites, particles, papers and the like typically used by those of skill in the art to sequester molecules. The solid phase can be non-porous or porous. Suitable solid phases include those developed and/or used as solid phases in solid phase binding assays. See, e.g., chapter 9 of Immunoassay, E. P. Dianiandis and T. K. Christopoulos eds., Academic Press: New York, 1996, hereby incorporated by reference. Examples of suitable solid phases include membrane filters, cellulose-based papers, beads (including polymeric, latex and paramagnetic particles), glass, silicon wafers, microparticles, nanoparticles, TentaGels, AgroGels, PEGA gels, SPOCC gels, and multiple-well plates. See, e.g., Leon et al., Bioorg. Med. Chem. Lett. 8: 2997, 1998; Kessler et al., Agnew. Chem. Int. Ed. 40: 165, 2001; Smith et al., J. Comb. Med. 1: 326, 1999; Orain et al., Tetrahedron Lett. 42: 515, 2001; Papanikos et al., J. Am. Chem. Soc. 123: 2176, 2001; Gottschling et al., Bioorg. Med. Chem. Lett. 11: 2997, 2001.

Surfaces such as those described above may be modified to provide linkage sites, for example by bromoacetylation, silation, addition of amino groups using nitric acid, and attachment of intermediary proteins, dendrimers and/or star polymers. This list is not meant to be limiting, and any method known to those of skill in the art may be employed.

Detectable Label Conjugates

Biological assays require methods for detection, and one of the most common methods for quantitation of results is to conjugate an enzyme, fluorophore or other detectable label to the molecule under study (e.g., using one or more analogs of the invention), which may be immobilized for detection by a receptor molecule that has affinity for the molecule. Alternatively, the receptor to the molecule under study (e.g., an antibody or binding fragment thereof made or selected using the analogs or conjugates of the invention) may be conjugated to an enzyme, fluorophore or other detectable label. Enzyme conjugates are among the most common conjugates used. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g, biotin, digoxigenin, maltose, oligohistidine, 2,4-dintrobenzene, phenylarsenate, ssDNA, dsDNA, etc.).

Particularly preferred detectable labels are fluorescent latex particles such as those described in U.S. Pat. Nos. 5,763,189, 6,238,931, and 6,251,687; and International Publication WO95/08772, each of which is hereby incorporated by reference in its entirety. Exemplary conjugation to such particles is described hereinafter.

A list of preferred embodiments follows:

Embodiment 1. A compound or salt thereof, said compound having a general formula:

Embodiment

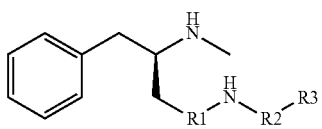

wherein

R1 is optionally substituted $C_{1-6}$ alkyl, wherein substitution(s), when present, may be independently selected from the group consisting of —$NO_2$, —$NH_2$, —OH, =O, —COOR' where R' is H or lower alkyl, —$CH_2OH$, and —$CONH_2$, R2 is peptide of m amino acid residues, an alkylene oxide of m alkylene oxide monomers, or $(CH_2)_m$, where m=2 to 6; and R3 is a linkage chemistry which provides a terminal functional moiety selected from the group consisting of protected or unprotected sulfhydryl moieties, protected or unprotected amine moieties, protected or unprotected hydroxyl moieties, primary amine-reactive moieties, sulfhydryl-reactive moieties, photoreactive moieties, carboxyl-reactive moieties, arginine-reactive moieties, and carbonyl-reactive moieties.

Embodiment 2. A compound or salt thereof according to embodiment 1, wherein R1 is —$(CH_2)_n$—, wherein n is 1 to 6.

Embodiment 3. A compound or salt thereof according to embodiment 1 or 2, wherein R2 is —$(O—CH_2—CH_2)_p$—, wherein p is 1 to 6.

Embodiment 4. A compound or salt thereof according to embodiment 1 or 2, wherein R2 is -Gly-Gly-, -Gly-Ala-, -Ala-Gly-, -Pro-Gly-, -Gly-Pro-, -Ala-Ala-, -Ala-Pro-, or -Pro-Ala-.

Embodiment 5. A compound or salt thereof according to one of embodiments 1-4, wherein R3 is a functional moiety selected from the group consisting of protected or unprotected sulfhydryl moieties, protected or unprotected amine moieties, protected or unprotected hydroxyl moieties, primary amine-reactive moieties, sulfhydryl-reactive moieties, photoreactive moieties, carboxyl-reactive moieties, arginine-reactive moieties, and carbonyl-reactive moieties.

Embodiment 6. A compound or salt thereof according to one of embodiments 1-4, wherein R3 is selected from the group consisting of a maleimide, an alkyl halide, an aryl halide, an alpha-haloacyl, an activated aryl, a pyridyl disulfide, a carbonyl, a carboxyl, a thiol, a thioester, disulfide, a N-hydroxy-succinimide, or a cyclic thiolactone.

Embodiment 7. A compound or salt thereof according to embodiment 6, wherein the compound has the structure

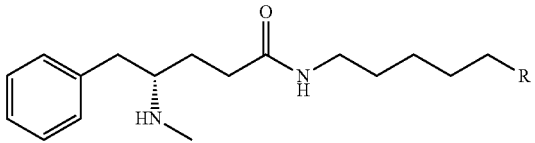

where R is a maleimide, an alkyl halide, an aryl halide, an alpha-haloacyl, an activated aryl, a pyridyl disulfide, a carbonyl, a carboxyl, a thiol, a thioester, disulfide, a N-hydroxy-succinimide, or a cyclic thiolactone.

Embodiment 8. A compound according to embodiment 7, wherein the compound is

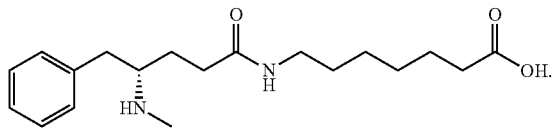 [SMILES: CN[C@@H](CCC(=O)NCCCCCCC(=O)O)Cc1ccccc1]

Embodiment 9. A conjugate comprising one or more compounds according to one of embodiments 1-8 covalently bound through the functional moiety on the compound(s) to a corresponding coupling site on a protein, polypeptide, detectable label, nucleic acid, or solid phase.

Embodiment 10. A conjugate according to embodiment 9, wherein the functional moiety is a sulfhydryl-reactive moiety.

Embodiment 11. A conjugate according to embodiment 10, wherein said sulfhydryl-reactive moiety is a maleimide.

Embodiment 12. A conjugate according to embodiment 10, wherein said sulfhydryl-reactive moiety is an alkyl halide, an aryl halide, an acryl, or an α-haloacyl, wherein the sulfhydryl-reactive moiety reacts with sulfhydryls to form thiol ether bonds.

Embodiment 13. A conjugate according to embodiment 12, wherein the functional moiety is a carbonyl-reactive moiety.

Embodiment 14. A conjugate according to one of embodiments 9-13, wherein said detectable label is selected from the group consisting of a hapten carrier protein comprising a T-helper epitope, an enzyme, a fluorophore, biotin, avidin, streptavidin, digoxigenin, maltose, oligohistidine, 2,4-dintrobenzene, phenylarsenate, a metal, a fluorescent or colored microsphere, a fluorescent particle, and a colored latex particle.

Embodiment 15. A conjugate according to according to embodiment 14, wherein said hapten carrier protein comprising a T-helper epitope is selected from the group consisting of keyhole limpet hemocyanin, bovine serum albumin, thyroglobulin, thioredoxin, ovalbumin, lysozyme, diphtheria antigen DT, diphtheria antigen CRM197 and tetanus toxoid.

Embodiment 16. A method of preparing a conjugate, comprising:

contacting one or more compounds of one of embodiments 1-8 with a protein, polypeptide, detectable label, nucleic acid, or solid phase under conditions to provide covalent coupling of said compound(s) to said protein, polypeptide, detectable label, nucleic acid, or solid phase through a reactive moiety on the compound(s).

Embodiment 17. A method according to embodiment 16, wherein said compound(s) comprise a protected reactive moiety, and said method further comprises deprotecting said reactive moiety following, or together with, said contacting step.

Embodiment 18. A method according to embodiment 16 or 17, wherein said method further comprises introducing said one or more coupling sites corresponding to the reactive moiety into said protein, polypeptide, detectable label, nucleic acid, or solid phase prior to said contacting step.

Embodiment 19. A method according to embodiment 18, wherein said reactive moiety is a sulfhydryl-reactive moiety, and said introducing step comprises coupling of said protein, polypeptide, detectable label, nucleic acid, or solid phase to one or more bivalent crosslinkers comprising said one or more sulfhydryl-reactive moieties.

Embodiment 20. A method of stimulating an immune response to methamphetamine, comprising:
immunizing an animal with a conjugate of one of embodiments 9-15.

Embodiment 21. A method according to embodiment 20, wherein the animal is a human.

Embodiment 22. A vaccine composition consisting of a hapten conjugated to a carrier; a particulate carrier vehicle; and one or more immunostimulatory adjuvant molecules.

Embodiment 23. The vaccine composition of embodiment 22, wherein the carrier is tetanus toxoid, diphtheria toxin CRM or thioredoxin.

Embodiment 24. The vaccine composition according to one of embodiments 22-24, wherein the particulate carrier vehicle is aluminum hydroxide or aluminum phosphate.

Embodiment 25. A vaccine composition according to one of embodiments 22-24, wherein the particulate carrier vehicle is a liposome.

Embodiment 26. A vaccine composition according to embodiment 25, wherein the liposome comprises phosphatidylcholine, a sterol, phosphatidylglycerol or phosphatidylethanolamine.

Embodiment 27. A vaccine composition according to one of embodiments 22-24, wherein the particulate carrier vehicle is an emulsion.

Embodiment 28. A vaccine composition according to one of embodiments 22-27, wherein the immunostimulatory adjuvant molecules comprise a Toll-like Receptor (TLR) agonist.

Embodiment 29. A vaccine composition according to one of embodiments 22-28, wherein the immunostimulatory adjuvant molecules comprise a STING agonist.

Embodiment 30. A vaccine composition according to one of embodiments 22-29, wherein the immunostimulatory adjuvant molecules comprise a C-type lectin receptor (CLR) agonist.

Embodiment 31. A vaccine composition according to embodiment one of embodiments 22-30, wherein the immunostimulatory adjuvant molecules comprise a NOD-like receptor (NLR) agonist.

Embodiment 32. A vaccine composition according to one of embodiments 22-31, wherein the immunostimulatory adjuvant molecules comprise a TLR2 agonist.

Embodiment 33. A vaccine composition according to one of embodiments 22-32, wherein the immunostimulatory adjuvant molecules comprise a TLR3 agonist.

Embodiment 34. A vaccine composition according to one of embodiments 22-33, wherein the immunostimulatory adjuvant molecules comprise a TLR4 agonist.

Embodiment 35. A vaccine composition according to one of embodiments 22-34, wherein the immunostimulatory adjuvant molecules comprise a TLR5 agonist.

Embodiment 36. A vaccine composition according to one of embodiments 22-35, wherein the immunostimulatory adjuvant molecules comprise a TLR7/8 agonist.

Embodiment 37. A vaccine composition according to one of embodiments 22-36, wherein the immunostimulatory adjuvant molecules comprise a TLR9 agonist.

Embodiment 38. A vaccine composition according to one of embodiments 22-37, wherein the immunostimulatory adjuvant molecules comprise a cyclic dinucleotide.

Embodiment 39. A vaccine composition according to one of embodiments 22-38, wherein the immunostimulatory adjuvant molecules comprise a muramyl di- or tri-peptide.

Embodiment 40. A vaccine composition according to one of embodiments 22-39, wherein the immunostimulatory adjuvant molecules comprise trehalose dibehenate.

Embodiment 41. A vaccine composition according to according to one of embodiments 22-40, wherein the hapten is a methamphetamine hapten.

Embodiment 42. A vaccine composition according to according to one of embodiments 22-40, wherein the hapten is an opioid hapten.

Embodiment 43. A vaccine composition according to according to one of embodiments 22-40, wherein the hapten is a nicotine hapten.

Embodiment 44. A vaccine composition according to according to one of embodiments 22-40, wherein the hapten is a cocaine hapten.

Embodiment 45. A vaccine composition according to according to one of embodiments 22-44, wherein the hapten is conjugated to the carrier via a linker.

Embodiment 46. A vaccine composition according to embodiment 45, wherein the linker comprises a peptide.

Embodiment 47. A vaccine composition according to embodiment 45 or 46, wherein the linker comprises an alkyl chain.

Embodiment 48. A vaccine composition according to one of embodiments 45-47, wherein the linker is polyethylene glycol.

Embodiment 49. A vaccine composition according to one of embodiments 22-48, wherein the hapten conjugated to a carrier is a conjugate according to one of embodiments 7-13.

Embodiment 50. A method of stimulating an immune response to methamphetamine, comprising:
immunizing an animal with a vaccine composition of one of embodiments 22-49.

Embodiment 51. A method according to embodiment 50, wherein the animal is a human.

EMBODIMENT EXAMPLE 1

Figure 3:
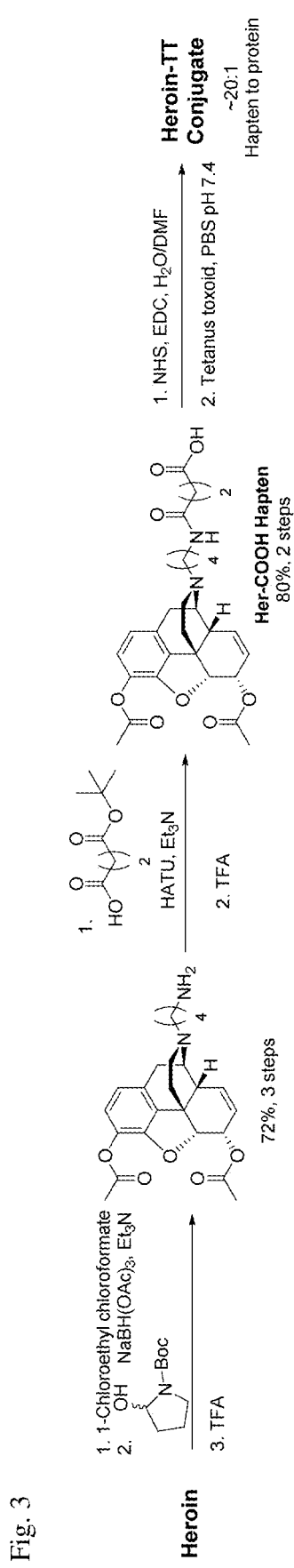
FIG. 3 depicts a scheme for preparation of A Heroin-COOH hapten/carrier (e.g., TT) conjugate.

In this example, a heroin hapten (Her-COOH) conjugated to a scaffold protein (tetanus toxoid, TT; FIG. 3) and adjuvanted with alum and CpG ODN 1826 stimulated effective anti-heroin immune responses. Candidate formulations were also prepared with CRM197 (CRM), a non-toxic diphtheria toxin mutant, widely used as a scaffold protein in conjugate vaccines and yeast virus dsRNA, a Toll-like receptor (TLR) 3 agonist. These components were then tested in mouse antinociception models to demonstrate efficacy.

Briefly, TT (UMass Biologics) or CRM (Fina Biosolutions) was dialyzed into phosphate buffered saline, pH 7.4 (PBS). The Her-COOH was dissolved in 1:9 $H_2O$/DMF (25 mM) and was activated with 6 equivalents of EDC-Cl and 6 equivalents of N-hydroxysuccinimide (NHS). Upon complete conversion to the NHS ester as judged by LCMS (typically 2 hours), 100 wt % activated hapten was added to 1.5 mg/mL TT or CRM to give 10 vol % DMF. Conjugations proceeded for 4 hours at room temperature and 18 hours at 4° C. with gentle mixing. Following hapten coupling, the resulting conjugate was dialyzed exhaustively at 4° C. for 36 hours. It should be noted that the CRM conjugate had a tendency to precipitate while the TT conjugate seemed to remain in solution much better. The conjugate was diluted 3:1 with glycerol and stored at −20° C. until immunization. The purification of yeast virus dsRNA followed similar procedures as described in Adler et al., (1976), and Hewitt and Adler (1982). The liposomes were prepared following commonly known procedures (Fujii G, Chang J-E, Coley T, and Steere B. (1997) *The formation of amphotericin B ion channels in lipid bilayers.* Biochemistry 36:4959-4968. PMID: 9125518).

Candidate vaccine formulations were tested in Swiss Webster mice. Six to eight week old outbred Swiss Webster male mice (n=4/group) were vaccinated subcutaneously (s.c.) on days 0, 14 and 28 with the candidate formulations listed in Table 1.

TABLE 1

Evaluation of Hero-TT vaccine formulations in Swiss Webster mice.

| Group | Vaccine | Hero-CRM/ Hero-TT (µg/dose) | alum (mg/dose) | Adjuvant | (Route) | Schedule: (days) | Injection Volume (µL) |
|---|---|---|---|---|---|---|---|
| 1 | Hero-CRM-LP-dsRNA | 50 µg Hero-CRM | 0 | LP 50 µg dsRNA | s.c./ s.c./ s.c. | 0, 14, 28 | 200 |
| 2 | Hero-CRM-dsRNA | 50 µg Hero-CRM | 0 | 50 µg dsRNA | s.c./ s.c./ s.c. | 0, 14, 28 | 200 |
| 3 | Hero-CRM-alum-dsRNA | 50 µg Hero-CRM | 1 | 50 µg dsRNA | s.c./ s.c./ s.c. | 0, 14, 28 | 200 |
| 4 | Hero-CRM-alum-CpG | 50 µg Hero-CRM | 1 | 50 µg CpG | s.c./ s.c./ s.c. | 0, 14, 28 | 200 |
| 5 | Hero-TT-alum-CpG | 50 µg Hero-TT | 1 | 50 µg CpG | s.c./ s.c./ s.c. | 0, 14, 28 | 200 |
| 6 | CRM-alum | 50 µg CRM | 1 | — | s.c./ s.c./ s.c. | 0, 14, 28 | 200 | s.c.—subcutaneous;
LP—liposome;
4 mice/group × 6 groups = 24 mice total

The test groups included: a 50 µg/dose of Her-COOH-conjugated CRM (Hero-CRM) with 50 µg dsRNA and 2.5 mg liposomes; a 50 µg/dose of Hero-CRM with 50 µg of dsRNA without alum; a 50 µg/dose of Hero-CRM with 50 µg dsRNA and 1 mg alum (Invivogen); and a 50 µg/dose of Hero-CRM with 50 µg CpG (ODN 1826; 5'-TC-CATGACGTTCCTGACGTT-3' with phosphorothioate backbone; Eurofins) and 1 mg alum. As a positive control, one group of mice received 50 µg/dose of Her-COOH conjugated TT (Hero-TT) with 50 µg CpG and 1 mg alum. As a negative control, one group of mice received 50 µg/dose of unconjugated CRM with 1 mg alum.

The mice were monitored for swelling, redness or formation of granulomas at the injection site. The mice were bled on days 21 and 42. The anti-heroin IgG antibody titers were determined by ELISA. On day 45, spinal (tail immersion, FIG. 1) and supraspinal (hot plate, FIG. 2) antinociceptive responses under escalating heroin doses were evaluated, to determine vaccine-mediated blockade of heroin psychoactivity. Both tests were performed at 54° C. Briefly, the hot plate test was measured by placing the mouse in an acrylic cylinder (14 cm diameter×22 cm) and timing latency to perform one of the following nociceptive responses: licking of hindpaw, shaking/withdrawal of hindpaw, or jumping. Immediately following a response, with typical baseline latency between 8-15 seconds and a 35 second cutoff to avoid tissue damage, mice were removed from the plate. The tail immersion test was administered by lightly restraining mice in a small pouch constructed from absorbent laboratory underpads and dipping 1 cm of the tip of the tail into a heated water bath, with the time to withdrawal timed. Typical baseline response was 1-2 seconds and a cutoff of 10 seconds was used to avoid tissue damage. Since tail immersion is a more reflexive behavior, testing order was always hot plate first followed by tail immersion, and then heroin in normal saline was immediately administered after completing both tests.

Roughly 15 min following each injection the tests were repeated, and if mice did not reach full antinociception for both tests, the animals continued to receive further cumulative drug injections and repeated testing until cutoff times were reached. The heroin doses tested were 2, 4, 6, 10, 14, 18, 22 and 26 mg/kg to generate full dose-response curves. Antinociceptive data was transformed from time to % maximum possible effect (% MPE), which is calculated as: % MPE=(test−baseline)/(cutoff−baseline)*100. This data was then fit using a log(agonist) vs. normalized response non-linear regression in GraphPad PRISM (left panels of FIGS. 1 and 2). These produced $ED_{50}$ values for each pain test for the individual treatment groups (middle panels of FIGS. 1 and 2), allowing calculation of potency ratios (right panels of FIGS. 1 and 2).

The ELISA titers showed that the alum formulations had significantly better titers than formulations without alum. The anti-nociception assay results (FIGS. 1 and 2) suggested that the dsRNA worked as well or possibly, better than CpG. The liposomal particles stimulated a reasonable immune response, but not as good as alum. Both the CRM and TT scaffold proteins stimulated potent immune responses.

EXAMPLE 2

In another study, CpG was combined with the dsRNA at a fixed dose of Hero-TT and alum as the nanoparticulate carrier. Also examined was the stability of the formulation by lyophilization. The candidate Hero-TT vaccine formulations were tested in 6-8 week old male Swiss Webster mice (n=4-6/group). The mice were vaccinated subcutaneously (s.c.) or intraperitoneally (i.p.) on weeks 0, 2 and 4, with the formulation listed in Table 2.

TABLE 2

Evaluation of Hero-TT formulations in Swiss Webster mice.

| Group | Vaccine | Hero-TTx (per dose) | Adjuvant (per dose) | Route | Schedule (days) | Formulation |
|---|---|---|---|---|---|---|
| 1 | Lyo-Hero-TT-dsRNA-CpG | 50 µg | 50 µg dsRNA + 50 µg CpG + 1 mg alum | s.c./ s.c./ s.c. | 0, 2, 4 | Lyophilized and reconstituted |
| 2 | Hero-TT-dsRNA-CpG | 50 µg | 50 µg dsRNA + 50 µg CpG + 1 mg alum | s.c./ s.c./ s.c. | 0, 2, 4 | Non-lyophilized |

TABLE 2-continued

Evaluation of Hero-TT formulations in Swiss Webster mice.

| Group | Vaccine | Hero-TTx (per dose) | Adjuvant (per dose) | Route | Schedule (days) | Formulation |
|---|---|---|---|---|---|---|
| 3 | Hero-TT-dsRNA | 50 µg | 50 µg dsRNA + 1 mg alum | s.c./ s.c./ s.c. | 0, 2, 4 | Non-lyophilized |
| 4 | Hero-TT-CPG | 50 µg | 50 µg CpG + 1 mg alum | s.c./ s.c./ s.c. | 0, 2, 4 | Non-lyophilized |
| 5 | Hero-TT-CPG (i.p.) | 50 µg | 50 µg CpG + 1 mg alum | i.p./ i.p./ i.p. | 0, 2, 4 | Non-lyophilized |
| 6 | TT-alum (vehicle) | 50 µg TT | 1 mg alum | s.c./ s.c./ s.c. | 0, 2, 4 | Non-lyophilized | s.c.—subcutaneous;
i.p.—intraperitoneally

Figure 4:
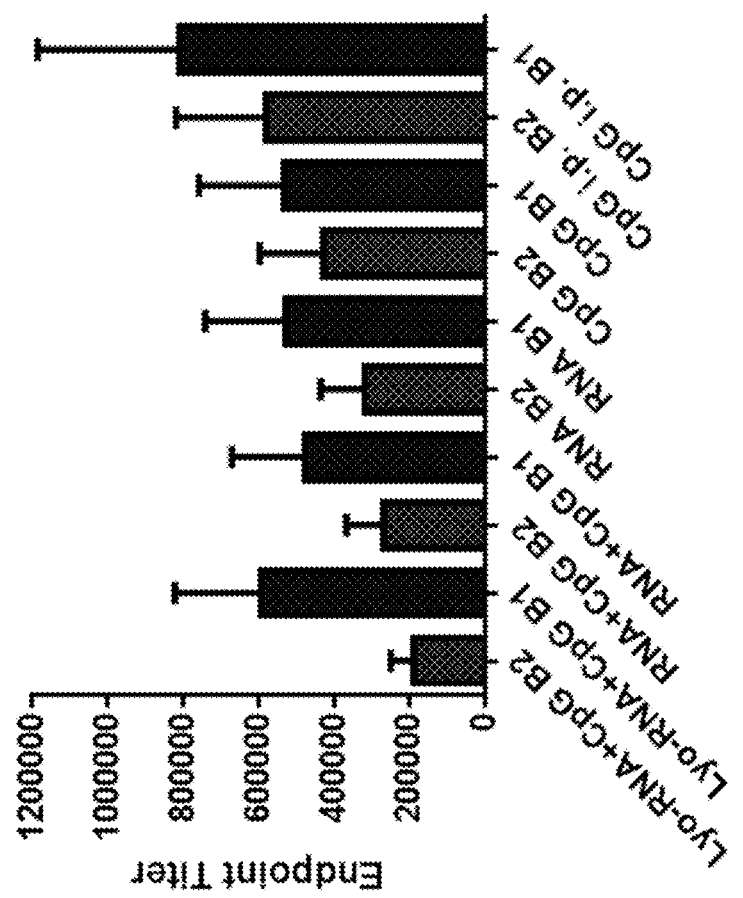
FIG. 4 depicts IgG titer of Heroin-TT vaccinated mice by ELISA from serum collected at 6 weeks (B1) and 10 weeks (B2).
Figure 5:
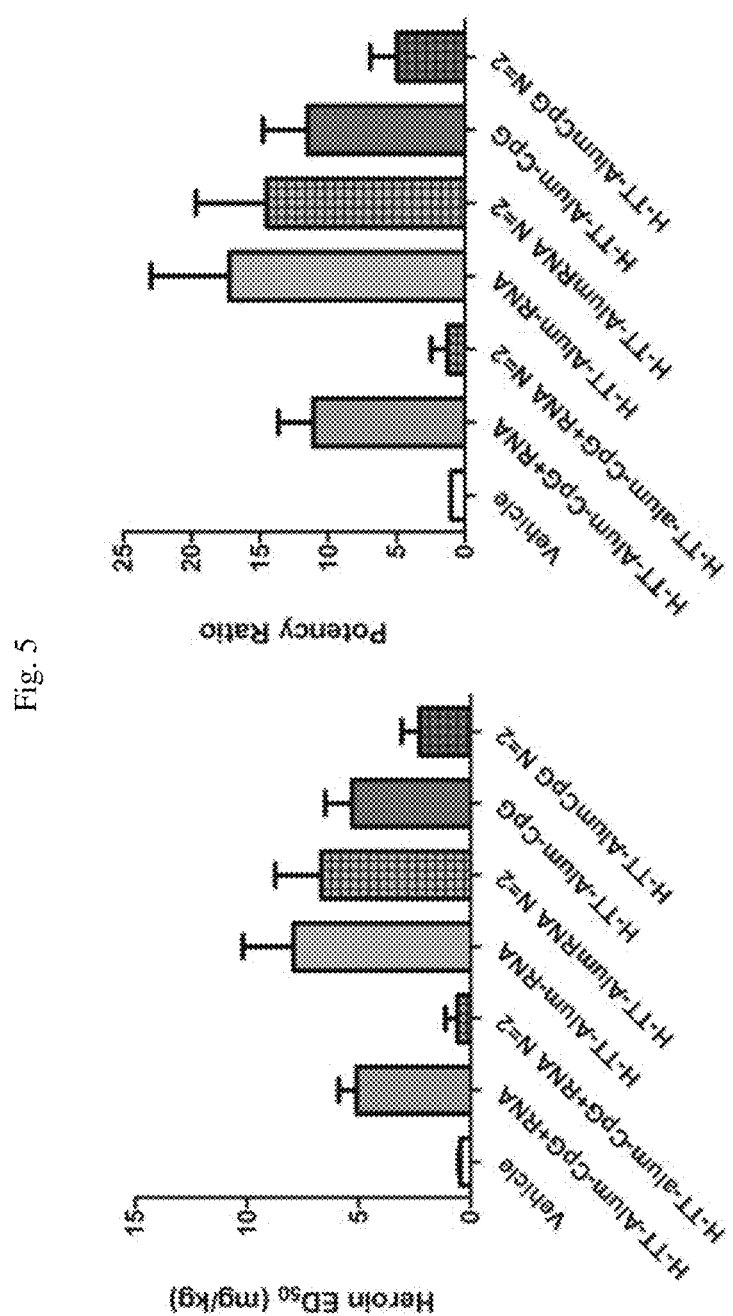
FIG. 5 depicts supraspinal (left) and spinal (right) antinociceptive responses of Heroin-TT formulations in vaccinated mice, measured at 6 weeks (N=1) and 10 weeks (N=2).

Tail vein bleeds were taken on weeks 6 and 10, and the IgG antibody geometric mean endpoint titers were determined by ELISA (FIG. 4). Five days following the week 6 and week 10 tail vein bleeds, the mice were tested for cumulative heroin response in supraspinal (hot plate, FIG. 5) and spinal (tail immersion) behavioral tests.

Figure 6:
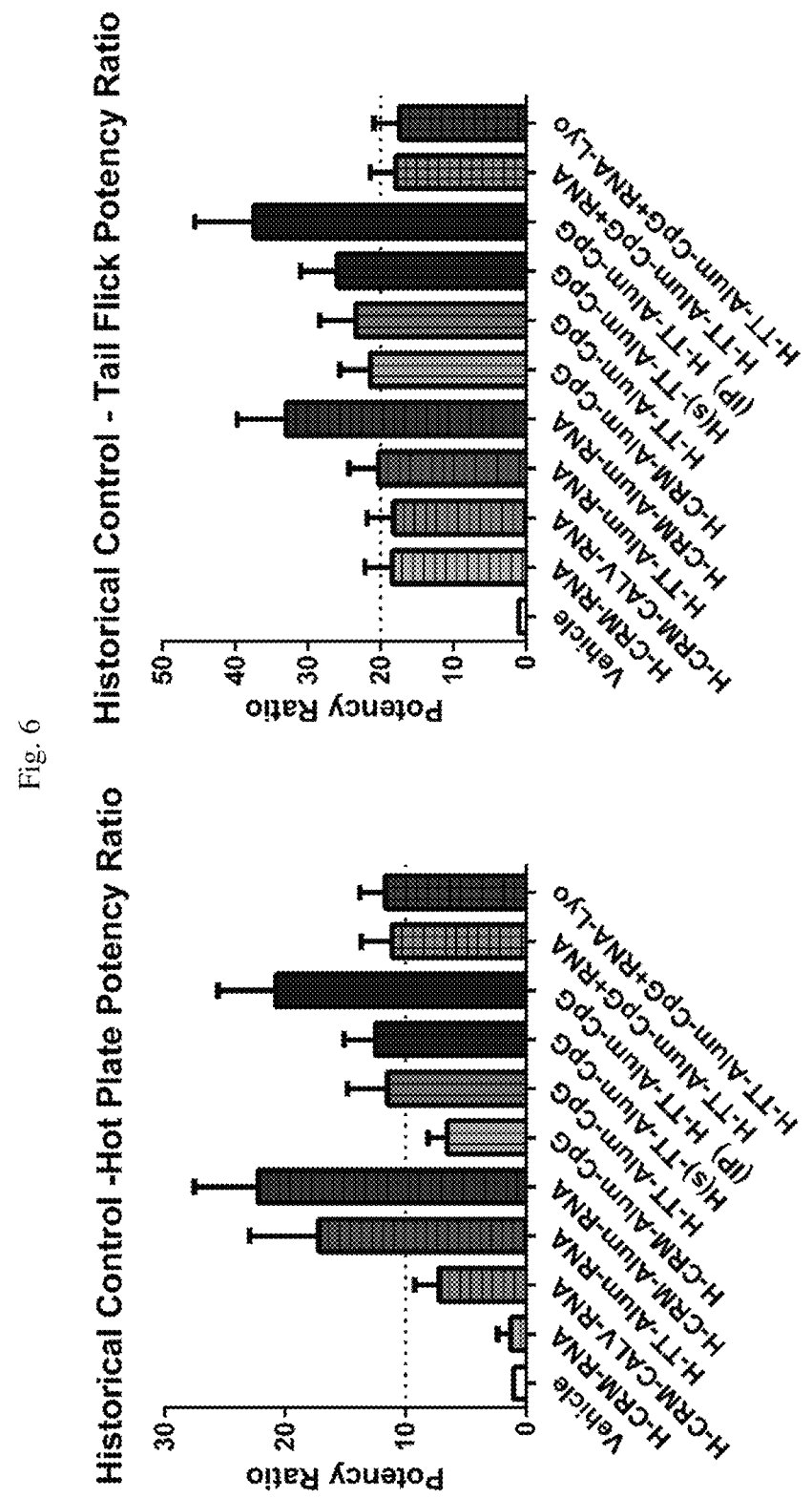
FIG. 6 depicts a comparison of the potency ratio of supraspinal (left) and spinal (right) antinociceptive responses of all Heroin-TT formulations.

A comparison of the potency ratio of the supraspinal and tail immersion behavioral tests between this experiment and the initial screening experiment is presented in FIG. 6.

The results from this study confirmed the results showing that the combination of alum and dsRNA stimulated antibody titers (>200,000) that were sufficient to perform very well in the antinociception assays. Further, the antibody levels remained higher than the other groups at the 10 week timepoint suggesting that the dsRNA stimulates a longer lasting antibody response. The addition of CpG to the dsRNA/alum formulation did not improve the immune response; however, it may be that the combined doses were simply to high to observe an increase in the immune response. The lyophilized samples maintained their potency; no loss of immunostimulatory activity was observed upon reconstitution and testing.

EXAMPLE 3

Figure 2:
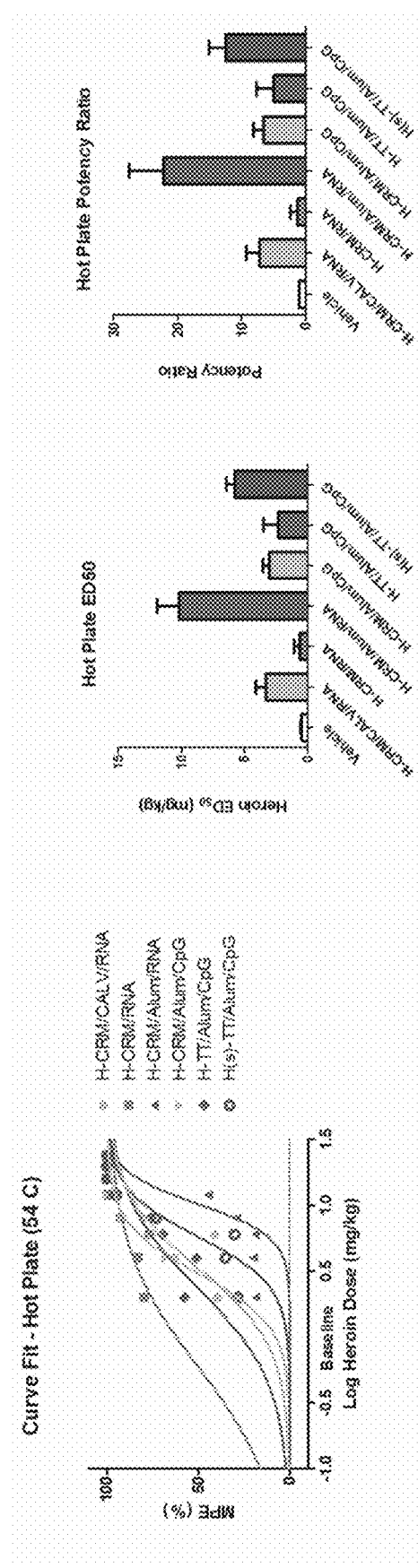
FIG. 2 depicts supraspinal antinociceptive responses to Hero-TT vaccine formulations measured at 45 days post-boost.

Hero-CRM-dsRNA formulated with liposomes had been shown to stimulate reasonably good immune responses as shown in Example 1 (see FIGS. 1 and 2). In another study, we investigated the potency of Hero-TT formulated with dsRNA with either liposomes or alum (Table 3).

TABLE 3

Testing of Hero-TT vaccine formulation in Swiss Webster mice.

| Group | Vaccine | Hero-TTx (per dose) | Adjuvant (per dose) | Route | Schedule (weeks) |
|---|---|---|---|---|---|
| 1 | Hero-TT-dsRNA-alum-LP | 50 µg | 50 µg dsRNA + 0.2 mg alum | s.c./s.c./s.c. | 0, 2, 4 |
| 2 | Hero-TT-dsRNA-LP | 50 µg | 50 µg dsRNA | s.c./s.c./s.c. | 0, 2, 4 |
| 3 | Hero-TT-LP | 50 µg | — | s.c./s.c./s.c. | 0, 2, 4 | s.c.—subcutaneous;
LP—liposomes

Figure 7:
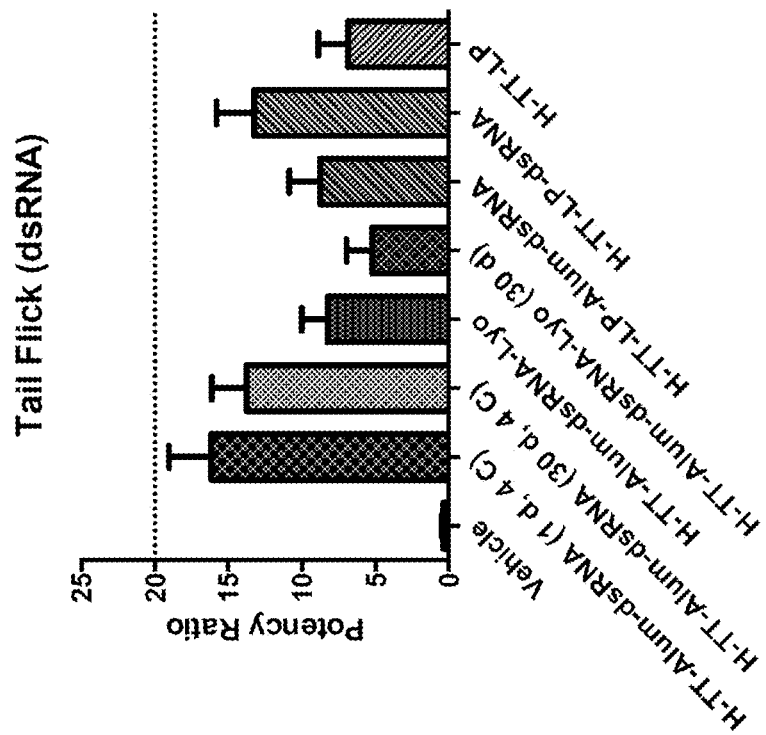
FIG. 7 depicts a comparison of the potency ratio of supraspinal (left) and spinal (right) antinociceptive responses of Heroin-TT formulations ("LP" indicates liposomes).
Figure 7:
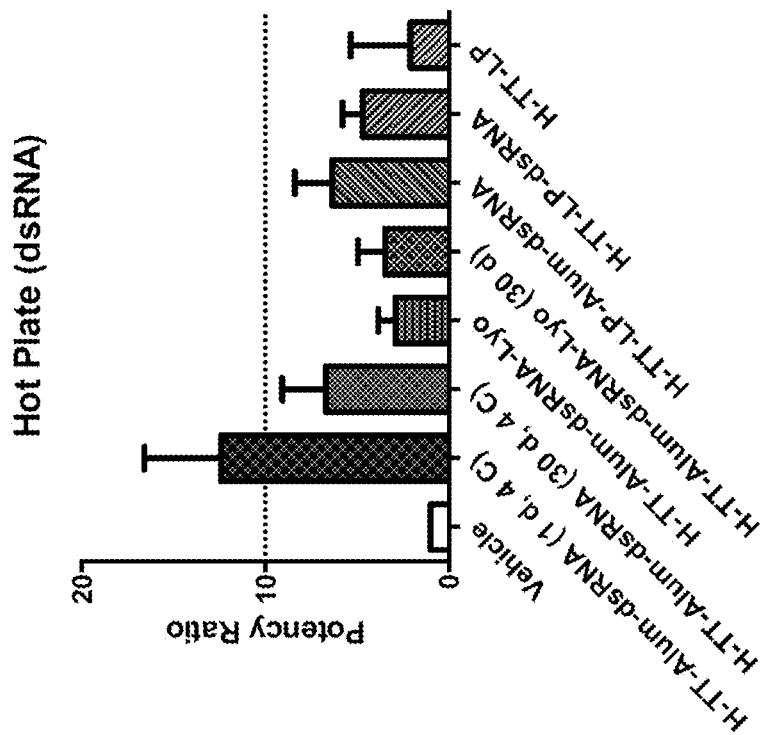
Figure 8:
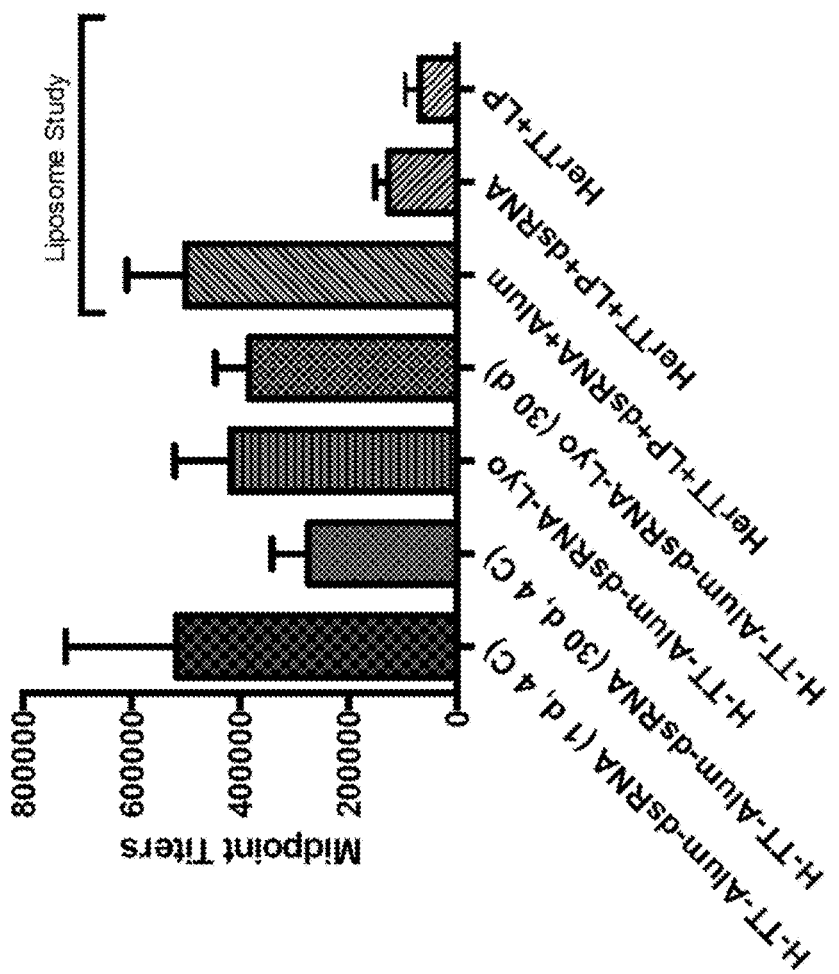
FIG. 8 depicts IgG titer of Heroin-TT formulations ("LP" indicates liposomes).

The Hero-TT-dsRNA liposome formulations were screened in 6-8 week old male Swiss Webster mice (n=5/group). The vaccines were injected subcutaneously (s.c.) on weeks 0, 2 and 4; the tail vein bleeds were taken for IgG titers (FIG. 8); and the mice were tested for cumulative heroin response in supraspinal (hot plate, FIG. 7, left) and spinal (tail immersion, FIG. 7, right) behavioral tests, as described above.

The antibody titer results show that the Hero-TT-dsRNA alum formulated in combination with liposomes did not elicit appreciably higher antibody titers compared to the Hero-TT-dsRNA-alum control (FIG. 6). While the Hero-TT-dsRNA formulation did not induce a relatively high level of titer (FIG. 6), the potency ratio, especially in the tail flick assay, was comparable to the samples formulated with alum (FIG. 7) suggesting that the antibodies that were stimulated had a much higher affinity for heroin.

EXAMPLE 4

Figure 9:
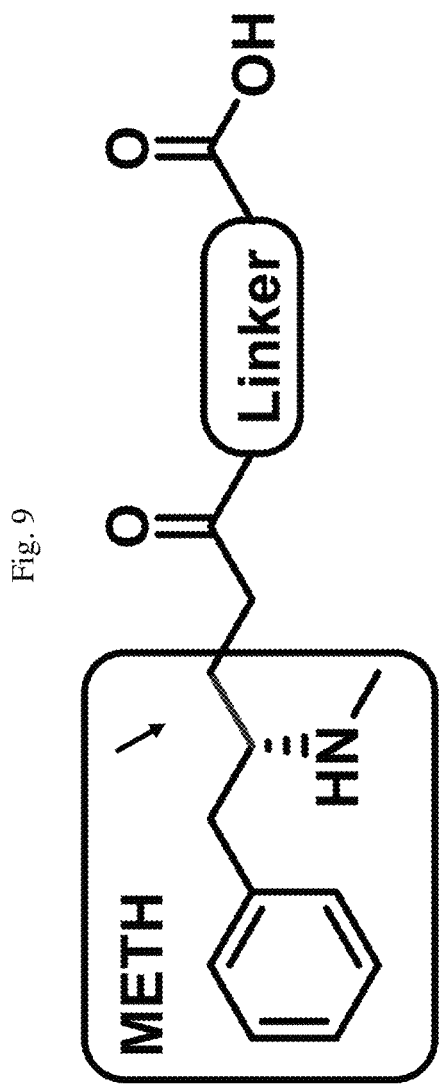
FIG. 9 depicts design of a methamphetamine hapten.
Figure 10:
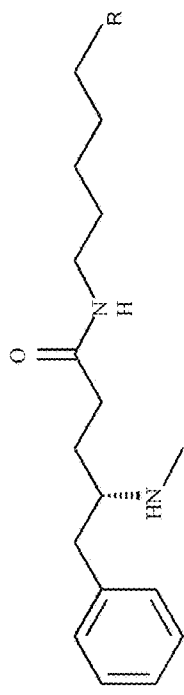
FIG. 10 depicts preferred methamphetamine haptens and their reactive groups for preparing conjugates of the invention
Figure 11:
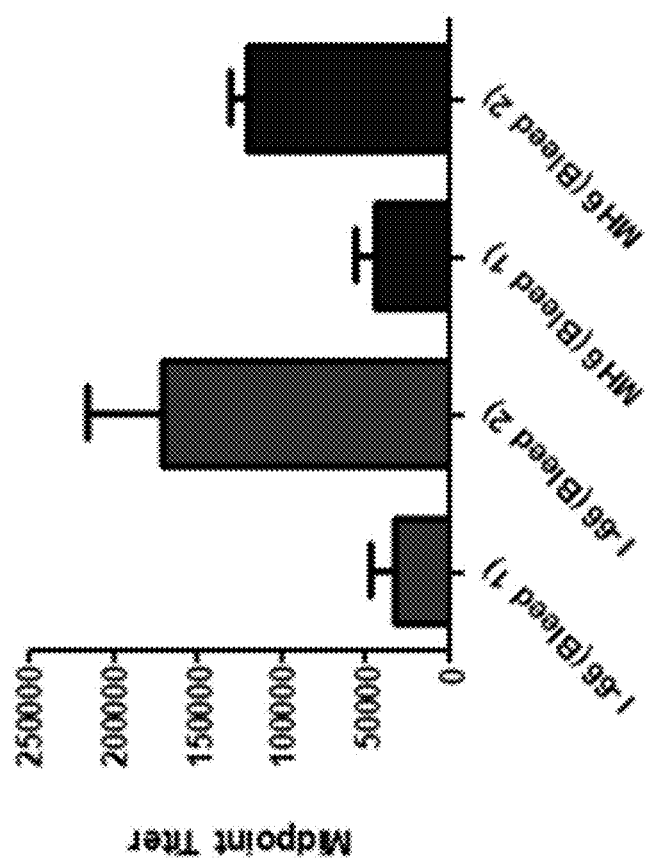
FIG. 11 depicts immunization results for a methamphetamine hapten (1-66) as compared to a prior art methamphetamine hapten (MH6).

A methamphetamine hapten was designed as shown in FIG. 9. In the METH hapten (1-66), the linker is attached to the hapten at the point indicated by the arrow, and can be conjugated to a scaffold protein through coupling to reactive groups on the surface of the protein scaffold. For purposes of illustration only, a carboxylic acid group is shown. However, it should be understood by one skilled in the art that other reactive groups such as those herein above may be employed. Such reactive groups are depicted in FIG. 10.

In this example, the METH hapten (1-66) was conjugated to a scaffold protein (tetanus toxoid, TT; FIG. 3) and adjuvanted with alum and CpG ODN 1826 stimulated effective anti-heroin immune responses. These components were then tested in a mouse model to demonstrate the stimulation of anti-methamphetamine antibody production and efficacy.

Briefly, TT (UMass Biologics) was dialyzed into phosphate buffered saline, pH 7.4 (PBS). The I-66 was dissolved in 1:9 $H_2O$/DMF (25 mM) and was activated with 6 equivalents of EDC-Cl and 6 equivalents of N-hydroxysuccinimide (NHS). Upon complete conversion to the NHS ester as judged by LCMS (typically 2 hours), 100 wt % activated hapten was added to 1.5 mg/mL TT to give 10 vol % DMF. Conjugations proceeded for 4 hours at room temperature and 18 hours at 4° C. with gentle mixing. Following I-66 hapten coupling, the resulting conjugate was dialyzed exhaustively at 4° C. for 36 hours. The conjugate was diluted 3:1 with glycerol and stored at −20° C. until immunization.

Candidate vaccine formulations were tested in Swiss Webster mice. Six to eight

TABLE 4

Evaluation of METH-TT formulations in Swiss Webster mice.

| Group | Vaccine | METH-TTx (per dose) | Adjuvant (per dose) | Route | Days |
|---|---|---|---|---|---|
| 1 | I-66-TT-CpG-Alhydrogel | 75 µg I-66-TT | 50 µg CpG + 750 µg Alhydrogel | s.c./s.c./ s.c. | 0, 14, 28 |
| 2 | MH-6-TT-CpG-alum | 75 µg MH-6-TT | 50 µg CpG + 750 µg alum | s.c./s.c./ s.c. | 0, 14, 28 |
| 3 | TT-alum | 75 µg TT | 750 µg alum | s.c./s.c./ s.c. | 0, 14, 28 | s.c.—subcutaneous week old outbred Swiss Webster male mice (n=6/group) were vaccinated subcutaneously (s.c.) on days 0, 14 and 28 with the candidate formulations listed in Table 4. No adverse reactions to the vaccines were observed and all mice maintained a healthy weight throughout the vaccine trial. Serum was collected via retro-orbital bleed on days 21 and 35.

The test groups included: a 75 µg/dose of I-66 conjugated TT with 50 µg CpG (ODN 1826; 5'-TCCATGACGTTCCTGACGTT-3' with phosphorothioate backbone; Eurofins) and 750 µg Alhydrogel. As a positive control, one group of mice received 75 µg/dose of MH-6 conjugated TT (MH-6-TT) with 50 µg CpG and 750 µg alum. As a negative control, one group of mice received 75 µg/dose of unconjugated TT with 750 µg alum.

On day 42, vaccinated mice were assessed in a locomotion assay by acclimating them for 1 h in a plastic cage (10.5 in.×19 in.×8 in.) with clear ventilated acrylic top. Mice were then quickly removed and injected with saline or 0.5, 1, 2, or 4 mg/kg METH before being returned to their cages; cages were wiped down with dry paper towels to remove excess debris while mice were being injected. The mice were then returned to the cage to be recorded and tracked by overhead camera using ANY-Maze video tracking software (Stoelting Co., Wood Dale, Ill.). Sessions were run during the middle of the dark cycle in a 4.6×4.6 $m^2$ room with a single 30 W upward-directed light source, and then repeated on mice after a two-day washout period until all mice received all MA doses. Distance traveled (m) and time spent immobile (s; 80% pixel consistency for at least 5 s threshold) were measured and analyzed via Prism 6 software, using a two-way repeated-measures ANOVA with Bonferroni post-hoc corrected comparisons. Significance was set at a=0.05 and data is represented as mean±SEM.

The mice were monitored for swelling, redness or formation of granulomas at the injection site. The mice were bled on days 21 and 42. The anti-METH IgG antibody titers were determined by ELISA. On day 45, mice were given a 2 mg/kg dose of METH and their locomotor activity was monitored.

The ELISA titers showed that anti-METH antibody titers stimulated by the I-66 hapten were at least comparable to, and possibly greater than, the MH-6 hapten (J. Am. Chem. Soc. 133: 6587, 2011). The locomotor nociception assay results suggested that the I-66 hapten worked as well as, and possibly better than, MH-6.

EXAMPLE 5. REFERENCES

1. NIDA. Trends & Statistics. 2017; Available from: www.drugabuse.gov/related-topics/trends-statistics.
2. Feyerick, D. Heroin use on the rise in United States. 2014; Available from: http://news.msn.com/us/video?videoid=39e7416a-685b-452f-87ac-f1a3164e1052ap=False&src=v5:endslate:email:&from=email.
3. Marbella, J. Trying to prevent heroin deaths one shot at a time. The Baltimore Sun, 2014; Available from: http://www.baltimoresun.com/news/maryland/sun-investigates/bs-md-heroin-narcan-naloxone-20140906-story.html.
4. Results from the 2012 National Survey on Drug Use and Health: Summary of National Findings. 2014, Substance Abuse Mental Health Services Administration Center for Behavioral Health Statistics Quality, U.S. DEPARTMENT OF HEALTH AND HUMAN SERVICES.
5. Kilmer, B., et al., What America's Users Spend on Illegal Drugs: 2000-2010. 2014, RAND Corporation.
6. Heroin, in Research Report Series. 2014, National Institutes of Health. p. 1-8.
7. Mark, T. L., et al., The economic costs of heroin addiction in the United States. Drug Alcohol Depend, 2001. 61(2): p. 195-206.
8. Principles of Drug Addiction and Treatment. 2012, National Institute on Drug Abuse, National Institutes of Health, U.S. Department of Health and Human Services. p. 1-75.
9. Walsh, S. L., et al., The relative abuse liability of oral oxycodone, hydrocodone and hydromorphone assessed in prescription opioid abusers, in Drug and Alcohol Dependence. 2008. p. 191-202.
10. Comer, S. D., et al., Relative abuse liability of prescription opiods compared to heroin in morphine-maintained heroin abusers. Neuropsychopharmacology, 2008. 33(5): p. 1179-1191.
11. Rosenblum, A., et al., Prescription opioid abuse among enrollees into methadone maintenance treatment. Drug and Alcohol Dependence, 2007. 90(1): p. 64-71.
12. Jones, C. M., Heroin use and heroin use risk behaviors among nonmedical users of prescription opioid pain relievers—United States, 2002-2004 and 2008-2010. Drug Alcohol Depend, 2013. 132(1-2): p. 95-100.
13. Results from the 2011 National Survey on Drug Use and Health: Summary of National Findings. 2012, Substance Abuse and Mental Health Services Administration: Rockville, Md.
14. The DAWN Report: Highlights of the 2009 Drug Abuse Warning Network (DAWN) Findings on Drug-Related Emergency Department Visits. 2010, Substance Abuse and Mental Health Services Administration, Center for Behavioral Health Statistics and Quality: Rockville, Md.
15. Vongpatanasin, W., et al., Cocaine stimulates the human cardiovascular system via a central mechanism of action. Circulation, 1999. 100(5): p. 497-502.
16. Bertol, E., et al., Cocaine-related deaths: an enigma still under investigation. Forensic Sci. Int., 2008. 176(2-3): p. 121-123.
17. Association, A. H., 2005 American Heart Association guidelines for cardiopulmonary resuscitation and emergency cardiovascular care: Part 10.2: toxicology in ECC. Circulation, 2005. 112: p. IV126-IV132.
18. Menon, D. V., et al., Central sympatholysis as a novel countermeasure for cocaine-induced sympathetic activation and vasoconstriction in humans. J. Am. Coll. Cardiol., 2007. 50(7): p. 626-633.
19. Hollander, J. E., The management of cocaine-associated myocardial ischemia. N. Engl. J. Med., 1995. 333: p. 1267-1272.
20. Lange, R. A. and L. D. Hillis, Cardiovascular complications of cocaine use. N. Engl. J. Med., 2001. 345: p. 351-358.
21. McCord, J., et al., Management of cocaine-associated chest pain and myocardial infarction: a scientific statement from the American Heart Association Acute Cardiac Care Committee of the Council on Clinical Cardiology. Circulation, 2008. 117(14): p. 1897-1907.
22. WHO report on the global tobacco epidemic, 2011: warning about the dangers of tobacco. 2011, WHO: Geneva.
23. Maurice, T., et al., Sigma(1) (sigma(1)) receptor antagonists represent a new strategy against cocaine addiction and toxicity. Neurosci. Biobehav. Rev., 2002. 26(4): p. 499-527.
24. Reyes, S., et al., KATP channels confer survival advantage in cocaine overdose. Mol. Psychiatry, 2007. 12(12): p. 1060-1061.

25. Reyes, S., et al., Therapeutic benefit of a KATP-channel opening drug in cocaine toxicity. Clin. Pharmacol. Ther., 2005. 77: p. P99-P99.
26. Sharkey, J., et al., Cocaine binding at sigma receptors. Eur. J. Pharmacol., 1988. 149: p. 171-174.
27. Gonzales, R., L. Mooney, and R. A. Rawson, The Methamphetamine Problem in the United States. Annu. Rev. Public Health, 2010. 31(1): p. 385-398.
28. Quenzer, D. and Suo, S The Spread of Meth, The Oregonian; Available from: http://www.oregonlive.com/special/oregonian/meth/pdfs/1003meth_spread.pdf.
29. Nicosia, N., et al., The Economic Cost of Methamphetamine Use in the United States, 2005, in The Economic Cost of Methamphetamine Use in the United States, 2005. RAND Corporation, Santa Monica, C A, 2009.
30. Gonzalez Castro, F., et al., Cocaine and methamphetamine: differential addiction rates. Psychol Addict Behav, 2000. 14(4): p. 390-6.
31. Sulzer, D., et al., Mechanisms of neurotransmitter release by amphetamines: A review. Prog. Neurobiol., 2005. 75(6): p. 406-433.
32. Rawson, R. A., Center for Substance Abuse Treatment. Treatment for Stimulant Use Disorders. 1999, Substance Abuse and Mental Health Services Administration (US): Rockville (Md.).
33. Rawson, R. A., M. D. Anglin, and W. Ling, Will the methamphetamine problem go away? J. Addict. Dis., 2002. 21(1): p. 5-19.
34. Vocci, F. J. and N. M. Appel, Approaches to the development of medications for the treatment of methamphetamine dependence. Addiction, 2007. 102: p. 96-106.
35. Chen, Y.-H. and C.-H. Chen, The Development of Antibody-based Immunotherapy for Methamphetamine Abuse: Immunization, and Virus-Mediated Gene Transfer Approaches. Curr. Gene Ther, 2013. 13: p. 39-50.
36. Carroll, K. M. and L. S. Onken, Behavioral therapies for drug abuse. Am. J. Psychiatry, 2005. 162(8): p. 1452-1460.
37. McKetin, R., et al., Evaluating the impact of community-based treatment options on methamphetamine use: findings from the Methamphetamine Treatment Evaluation Study (MATES). Addiction, 2012. 107(11): p. 1998-2008.
38. Maglione, M., B. Chao, and M. D. Anglin, Correlates of outpatient drug treatment drop-out among methamphetamine users. J Psychoactive Drugs, 2000. 32(2): p. 221-8.
39. Miller, M. L., et al., A Methamphetamine Vaccine Attenuates Methamphetamine-Induced Disruptions in Thermoregulation and Activity in Rats. Biol. Psychiat., 2013. 73(8): p. 721-728.
40. Moreno, A. Y., A. V. Mayorov, and K. D. Janda, Impact of Distinct Chemical Structures for the Development of a Methamphetamine Vaccine. J. Am. Chem. Soc., 2011. 133(17): p. 6587-6595.
41. Rüedi-Bettschen, D., et al., Vaccination protects rats from methamphetamine-induced impairment of behavioral responding for food. Vaccine, 2013. 31(41): p. 4596-4602.
42. Shen, X. Y., et al., A vaccine against methamphetamine attenuates its behavioral effects in mice. Drug Alcohol Depen., 2013. 129(1-2): p. 41-48.
43. Byrnes-Blake, K. A., et al., Generation of anti-(+) methamphetamine antibodies is not impeded by (+)methamphetamine administration during active immunization of rats. Int. Immunopharmacol., 2001. 1(2): p. 329-338.
44. Carroll, F. I., et al., Synthesis of Mercapto-(+)-methamphetamine Haptens and Their Use for Obtaining Improved Epitope Density on (+)-Methamphetamine Conjugate Vaccines. J. Med. Chem., 2011. 54(14): p. 5221-5228.
45. Collins, K. C., et al., Lipid tucaresol as an adjuvant for methamphetamine vaccine development. Chem. Commun., 2014.
46. Duryee, M. J., et al., Immune responses to methamphetamine by active immunization with peptide-based, molecular adjuvant-containing vaccines. Vaccine, 2009. 27(22): p. 2981-2988.
47. Wong, S. S., Chemistry of protein conjugation and cross-linking. 1991, Boca Raton: CRC Press. 340 p.
48. Adler, J., H. A. Wood, and R. F. Bozarth, Virus-like particles from killer, neutral, and sensitive strains of *Saccharomyces cerevisiae*. J Virol, 1976. 17(2): p. 472-6.
49. Hewitt, C. W. and J. P. Adler, Murine immunosuppression with mycoviral dsRNA. Immunopharmacology, 1982. 5(2): p. 103-9.
50. Fujii, G., W. Ernst, and J. Adler-Moore, The VesiVax system: a method for rapid vaccine development. Front Biosci, 2008. 13: p. 1968-80.
51. Bremer, P. T., et al., Injection route and TLR9 agonist addition significantly impact heroin vaccine efficacy. Mol Pharm, 2014. 11(3): p. 1075-80.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

The invention claimed is:

1. A method of stimulating an immune response to methamphetamine, comprising:
   immunizing an animal by administering to the animal a conjugate comprising one or more compounds having a general formula:

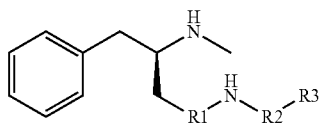

wherein
   R1 is —(O—CH$_2$—CH$_2$)$_p$—, wherein p is 1 to 6, or R1 is an optionally substituted C$_{1-6}$ alkyl, wherein substitution(s) are independently selected from the group consisting of —NO$_2$, —NH$_2$, —OH, =O, —COOR' where R' is H or lower alkyl, —CH$_2$OH, and —CONH$_2$,
   R2 is peptide of m amino acid residues, an alkylene oxide of m alkylene oxide monomers, or (CH$_2$)$_m$, where m=2 to 6; and
   R3 is selected from the group consisting of a protected or unprotected maleimide, alkyl halide, aryl halide, alpha-haloacyl, pyridyl disulfide, aldehyde, ketone, carboxyl, thiol, thioester, disulfide, N-hydroxy-succinimide, or cyclic thiolactone,
   or salts thereof, wherein the one or more compounds or salts thereof are covalently bound through R3 on the compound(s) to a corresponding coupling site on a protein, polypeptide, detectable label, nucleic acid, or solid phase to provide the conjugate.

2. A method according to claim 1, wherein the animal is a human.

3. A method according to claim 1, further comprising co-administering one or more immunostimulatory adjuvant molecules with the conjugate.

4. A method according to claim 3, wherein the animal is a human.

5. A method according to claim 1, wherein R2 is -Gly-Gly-, -Gly-Ala-, -Ala-Gly-, -Pro-Gly-, -Gly-Pro-, -Ala-Ala-, -Ala-Pro-, or -Pro-Ala-.

6. A method according to claim 1, wherein the compound has the structure

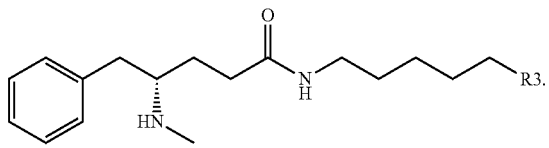

7. A method according to claim 1, wherein the compound has the structure

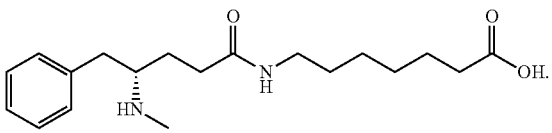 [SMILES: CN[C@@H](CCC(=O)NCCCCCCC(=O)O)Cc1ccccc1]

8. A method according to claim 1, wherein the protein, polypeptide, detectable label, nucleic acid, or solid phase is selected from the group consisting of a hapten carrier protein comprising a T-helper epitope, an enzyme, a fluorophore, biotin, avidin, streptavidin, digoxigenin, maltose, oligohistidine, 2,4-dintrobenzene, phenylarsenate, a metal, a fluorescent or colored microsphere.

9. A method according to according to claim 8, wherein said protein is selected from the group consisting of keyhole limpet hemocyanin, bovine serum albumin, thyroglobulin, thioredoxin, ovalbumin, lysozyme, diphtheria antigen DT, diphtheria antigen CRM197 and tetanus toxoid.

* * * * *